(12) United States Patent
Granger et al.

(10) Patent No.: US 7,887,754 B2
(45) Date of Patent: Feb. 15, 2011

(54) POLYMERIC SOLID SUPPORTS FOR CHROMATOGRAPHY NANOCOLUMNS

(75) Inventors: Jennifer H. Granger, Northborough, MA (US); Robert Plumb, Milford, MA (US)

(73) Assignee: Waters Technologies Corporation, Milford, MA (US)

( * ) Notice: Subject to any disclaimer, the term of this patent is extended or adjusted under 35 U.S.C. 154(b) by 1254 days.

(21) Appl. No.: 10/544,883

(22) PCT Filed: Feb. 6, 2004

(86) PCT No.: PCT/US2004/003484

§ 371 (c)(1),
(2), (4) Date: Jan. 20, 2006

(87) PCT Pub. No.: WO2004/071615

PCT Pub. Date: Aug. 26, 2004

(65) Prior Publication Data

US 2006/0144770 A1    Jul. 6, 2006

Related U.S. Application Data

(60) Provisional application No. 60/446,399, filed on Feb. 10, 2003, provisional application No. 60/445,725, filed on Feb. 7, 2003.

(51) Int. Cl.
*G01N 33/00*    (2006.01)

(52) U.S. Cl. .................................................. 422/101

(58) Field of Classification Search ................. 422/101
See application file for complete search history.

(56) References Cited

U.S. PATENT DOCUMENTS 2,676,182 A    4/1954    Daudt et al.

(Continued)

FOREIGN PATENT DOCUMENTS

WO    WO-99/29388    6/1999

(Continued)

OTHER PUBLICATIONS

Asiaie et al., J Chromatog A. (1998), 806, pp. 251.

(Continued)

*Primary Examiner*—Sam P Siefke
(74) *Attorney, Agent, or Firm*—Edwards Angell Palmer & Dodge LLP; Peter C. Lauro, Esq.; Nicholas J. DiCeglie, Jr., Esq.

(57) ABSTRACT

Nanocolumn chromatography devices useful, e.g., in CEC and nanoLC are disclosed. An exemplary chromatography device of the invention includes a nanocolumn, e.g., a capillary, packed with a particulate stationary phase material and a solid support. The solid support, or in situ frit, is adjacent to and integral with the stationary phase material. An in situ frit of the invention may be a mixture of the stationary phase material and a polymeric network of cross-linked poly(diorganosiloxane), e.g., poly(dimethylsiloxane), which may optionally be sintered. The invention also provides methods of making and using such devices.

120 Claims, 3 Drawing Sheets

U.S. PATENT DOCUMENTS

| | | | |
|---|---|---|---|
| 2,823,218 | A | 2/1958 | Speier et al. |
| 3,159,601 | A | 12/1964 | Ashby |
| 3,159,662 | A | 12/1964 | Ashby et al. |
| 3,220,972 | A | 11/1965 | Lamereaux |
| 3,419,593 | A | 12/1968 | Willing |
| 3,445,420 | A | 5/1969 | Kookootsedes et al. |
| 3,445,426 | A | 5/1969 | Lee |
| 3,723,497 | A | 3/1973 | Baney |
| 3,808,125 | A | 4/1974 | Good |
| 3,878,092 | A | 4/1975 | Fuller |
| 4,102,782 | A | 7/1978 | Saito et al. |
| 4,229,548 | A | 10/1980 | Sattlegger et al. |
| 4,346,610 | A | 8/1982 | Ishii et al. |
| 4,374,967 | A | 2/1983 | Brown et al. |
| 4,518,716 | A | 5/1985 | Lee et al. |
| 4,529,789 | A | 7/1985 | Kroupa |
| 4,544,681 | A | 10/1985 | Lee et al. |
| 4,572,918 | A | 2/1986 | Lee et al. |
| 4,636,316 | A | 1/1987 | Harris et al. |
| 4,793,920 | A | 12/1988 | Cortes et al. |
| 4,831,070 | A | 5/1989 | McInally et al. |
| 4,882,377 | A | 11/1989 | Sweet et al. |
| 5,071,769 | A | 12/1991 | Kundu et al. |
| 5,310,462 | A | 5/1994 | Chen |
| 5,310,463 | A | 5/1994 | Dadoo et al. |
| 5,312,535 | A | 5/1994 | Waska et al. |
| 5,332,795 | A | 7/1994 | Fujiki et al. |
| 5,342,492 | A | 8/1994 | Dadoo et al. |
| 5,364,521 | A | 11/1994 | Zimmermann |
| 5,371,163 | A | 12/1994 | Wilson |
| 5,378,334 | A | 1/1995 | Dadoo et al. |
| 5,571,853 | A | 11/1996 | Ikeno et al. |
| 5,637,135 | A | 6/1997 | Ottenstein et al. |
| 6,048,457 | A | 4/2000 | Kopaciewicz et al. |
| 6,139,733 | A | 10/2000 | Hargro et al. |
| 6,162,362 | A | 12/2000 | Ma et al. |
| 6,169,155 | B1 | 1/2001 | Alvarez et al. |
| 6,395,183 | B1 | 5/2002 | Valaskovic et al. |
| 7,250,214 | B2 * | 7/2007 | Walter et al. ................ 428/405 |
| 2002/0178797 | A1 | 12/2002 | Pawliszyn |
| 2002/0179513 | A1 | 12/2002 | Willis et al. |
| 2003/0021730 | A1 | 1/2003 | Muller et al. |
| 2003/0150811 | A1 | 8/2003 | Walter et al. |
| 2006/0219636 | A1 | 10/2006 | Plumb et al. |

FOREIGN PATENT DOCUMENTS

| | | |
|---|---|---|
| WO | WO-00/10675 | 3/2000 |
| WO | PCT/US00/03052 | 8/2000 |
| WO | WO-01/57516 | 8/2001 |
| WO | WO-01/68240 A2 | 9/2001 |
| WO | PCT/US02/25193 | 2/2003 |
| WO | PCT/US02/25250 | 3/2003 |

OTHER PUBLICATIONS

Dulay et al., Anal. Chem. (1998), 70, pp. 5103.
Goldstein et al., J. Mat. Sci. Letters. (1997), 16, pp. 310.
Leonard et al. J. Chrom. B. (1995(, 664, pp. 39.
Morris et al., Science, (1999), 284, pp. 622.
Tang et al., J. Chrom. A. (1999), 837, pp. 35.
Tang et al. J. Microcolumn Separations (2000), 12, pp. 6.
Ueno et al., Journal-Ceramic Society Japan, (2001), 109, pp. 210.
Xin et al., Electrophoresis, (1999), 20, pp. 67.
Yang et al., J Chrom. (1991), 544, pp. 233.
Zeng et al., Sensors and Actuators B, (2002), 82, pp. 209.
Chen, J-R., et al. Anal. Chem. (2001), 73, pp. 1987-1992.
Dulay, M. T. et al. Anal. Chem. (2001), 73, pp. 3921-3926.
Zeng, S. et al. Sensors and Actuators B, (2001), 79, pp. 107-114.
Kato, et al. J. Chromatography A. (2001), 924, pp. 187.
Colon, L. A. et al. J. Chromatography A, (2000), 887; pp. 43-53.
Chen, J-R., et al. Anal. Chem. (2000), 72, pp. 1224-1227.
Chirica, G. S. et al. Anal. Chem. (2000), 72, pp. 3605-3610.
Chirica, G. S. et al. Electrophoresis, (2000), 21, pp. 3093-3101.
Chirica, G. S. et al. Electrophoresis, (1999), 20, pp. 50-56.
Dadoo, et al. LC-GC (1997), 15, pp. 630.
Smith, R. M. et al. Pure Appl. Chem. (1997), 69:7, pp. 1475-1480.
Jorgenson, et al. J. Chromatog. (1981), 218, pp. 209.
Pretorius, et al. J. Chromatog. (1974), 99, pp. 23.

* cited by examiner

POLYMERIC SOLID SUPPORTS FOR CHROMATOGRAPHY NANOCOLUMNS

RELATED APPLICATIONS

This application is a U.S. national phase application, pursuant to 35 U.S.C. §371, of PCT international application Ser. No. PCT/US2004/003484 filed Feb. 6, 2004, designating the United States, which claims priority under 35 U.S.C. §119 to U.S. Provisional patent application Ser. No. 60/446,399 filed Feb. 10, 2003and to U.S. Provisional patent application Ser. No. 60/445,725 filed Feb. 7, 2003. The entire contents of the aforementioned patent applications are incorporated herein by this reference.

BACKGROUND OF THE INVENTION

Several contemporary methods exist for the analytical separation of components of a mixture. In general, a liquid sample containing compounds of interest is separated by partitioning between a mobile phase and a stationary phase, and the individual separated compounds are analyzed.

For example, electrophoresis, particularly capillary electrophoresis ("CE") is a method for separation of individual molecular species from a mixture by the application of an electric field. Separation of the molecules occurs because of their different rates of movement through the solution, the rate being influenced by pH of the solution, the mass, and charge of the molecule, and the strength and duration of the electric field. For example, a separation is typically performed in a capillary tube that is filled with an electrically conductive electrolyte solution and that is open on both ends. An electric field is applied by high voltage electrodes arranged at the ends of the capillary. Detection of separated molecules may be performed in the capillary, e.g., by laser irradiation of fluorescent molecules through a window on the outer surface of a capillary produced by removing the polyimide coating. See, e.g., U.S. Pat. Nos. 5,312,535, 5,364,521, and 5,310,462.

High performance liquid chromatography ("HPLC"), is another method that employs partitioning between a mobile liquid phase under high pressure and a stationary phase, for example silica-based columns, including bonded silica, and organic resins such as divinyl benzene. Of these, reverse phase silica-based columns are preferred because they have high separation efficiencies, are mechanically stable, and a variety of functional groups can be easily attached for a variety of column selectivities. Recently, miniature HPLC chromatography systems and techniques have been developed. These techniques use columns of smaller internal diameter than are usually used in conventional HPLC separations, and they only require samples of less than about 1 μL. These techniques are referred to by several names, including "micro liquid chromatography" (or "MLC"), "micro-high-performance LC" or simply "micro LC," "capillary LC," or "nanoLC" (i.e., the term used herein). U.S. Pat. Nos. 4,102,782, and 4,346,610.

A newer method is capillary electrochromatography ("CEC") in which an electric field is applied across capillary columns packed with microparticles and the resulting electroosmotic flow acts as a pump for chromatography. The technique combines the advantages of the high efficiency obtained with capillary electrophoretic separations and the general applicability of HPLC. CEC has the capability to drive the mobile phase through columns packed with chromatographic particles, especially small particles, when using electroosmotic flow. See, e.g., Colon, et al., J. Chromatog. 887, 43 (2000); Dadoo, et al., LC-GC 15, 630 (1997); Jorgenson, et al., J. Chromatog. 218, 209 (1981); Pretorius, et al., J. Chromatog. 99, 23 (1974); and U.S. Pat. Nos. 6,395,183, 5,378,334, 5,342,492, and 5,310,463. Generally, capillaries are packed, either electrokinetically or using a pump, with an appropriate stationary phase material, which may be a same stationary phase material commonly used in HPLC. The chromatography column generally comprises a fused silica capillary tube having a circular cross-section. A portion of the capillary column is packed with a stationary solid phase material (e.g., bonded silica particles about 1 to 3 μm in diameter) held in place with porous frits which are typically sintered silica particles disposed at the upstream (inlet) and downstream (outlet) ends of the column. Under the combined effects of mobile phase flow, ionic drift induced by the applied electric field, and the partitioning effect of the stationary phase, the mixture is separated. To avoid disturbing the stationary phase, detection and analysis of the various components of the mixture typically takes place in an unpacked, or open, portion of the capillary column adjacent the downstream end where the bands corresponding to the individual components of the mixture emerge from the packed capillary column.

The chromatography columns used in CEC, HPLC, and related analytical methods require for optimal performance a permeable containment devices to retain fluids or stationary phase material within a column, or to filter particles, e.g., particulate contaminants in analytical samples. Common containment devices include fiberglass packings, screens, and bonded particles, typically referred to as "frits."

There are many different methods of making frits but most techniques employ the consolidation of small particles by sintering or melting compressed particles of a known size together. In one typical method, an appropriate material is ground up into small pieces and screened for a selected size range of particles. The particles are then compressed together in a mold and heated to fuse the particles together, but not to melt or degrade the particles. After heating, the material is further processed by machining, and welding or gluing to an appropriate substrate. Another approach uses filaments, of either metals and plastics, that are randomly arranged, compressed, and fused together. Such filamentous frits are generally only appropriate for large (i.e., non-capillary) columns. Yet another approach uses screens to provide a containment device that serves as an alternate to frits, but screens generally have a lower limit of performance based on the size of the wire or filament used. However, screens offer low back pressure compared to frits. Colon, et al., J. Chromatog. 887, 43 (2000).

Neither the frit nor the screen offers an ideal structure for the containment of a packing or for providing a particle filter in applications that require small hole or pore sizes, particularly for a packed capillary column as used in either liquid chromatography ("LC") or capillary electrophoresis ("CE"). The conventional frit, because of the convoluted route of the pore including paths that contain lateral translations, has high back pressure. While a screen has low back pressure, the screen has a lower limit on pore size. Frits also cause a void volume that reduces the quality of chromatographic data, especially in smaller columns and in separations of small volumes in which the volume of the frit relative to the sample volume is considerable.

"Fritless" columns have been explored as an alternative to the shortcomings of frits and screens, particularly in CEC columns. For example, one report discloses in situ acrylate polymerization mediated by a free-radical mechanism. Chirica, et al., Anal. Chem. 72, 3605 (2000). Other reports demonstrate the in situ synthesis of frits by sintering of silicates. Chirica, et al., Electrophoresis 20, 50 (1999); Chirica, et al., Electrophoresis 21, 3093 (2000); see also Zeng, et al., Sensors and Actuators B 79, 107 (2001). Although these columns are mechanically stable, it is difficult to achieve a stable baseline. Others have attempted to make frits by in situ photopolymerization of acrylates. See Chen, et al., Anal. Chem. 72, 1224 (2000); Dulay, et al., Anal. Chem. 73, 3921 (2001); Chen, et al., Anal. Chem. 73, 1987 (2001); Kato, et al., J. Chromatog. A, 924, 187 (2001). The polymer is thought to act as a "nanoglue" by immobilizing the particles of the stationary phase material. Such photopolymerization methods are limited to the manufacture of columns which are optically transparent.

SUMMARY OF THE INVENTION

The present invention overcomes some of the above-referenced shortcomings and provides improved nanocolumn chromatography devices useful, e.g., in CEC. An exemplary chromatography device of the invention includes a nanocolumn, e.g., a capillary, packed with a particulate stationary phase material and a solid support The solid support, which may be referred to as an "in situ frit" is adjacent to and integral with the stationary phase material. An "in situ frit" of the invention may be a mixture of the stationary phase material and a polymeric network of cross-linked poly(diorganosiloxane), e.g., poly(dimethylsiloxane), which may optionally be sintered. The invention also provides methods of making and using such devices.

Additionally, the present invention is directed to an in situ frit for immobilizing a stationary phase material in a chromatography nanocolumn comprising an intimate mixture of particles of a stationary phase material and a polymeric network of cross-linked poly(diorganosiloxane), wherein the particles are suspended in the network.

Likewise, the invention relates to a medium for molecular separations comprising a particulate stationary phase material, and an in situ frit adjacent to and integral with the stationary phase material. The in situ frit comprises an intimate mixture of particles of a stationary phase material and a polymeric network of cross-linked poly(diorganosiloxane), and the particles are suspended in the network.

In a further embodiment, the invention relates to a column chromatography device comprising a nanocolumn having a cylindrical interior for accepting a stationary phase, a particulate stationary phase material packed within the nanocolumn. The in situ frit is within the nanocolumn and adjacent to and integral with the stationary phase material. The in situ frit comprises an intimate mixture of particles of a stationary phase material and a polymeric network of cross-linked poly (diorganosiloxane), and the particles are suspended in the network.

The invention also pertains to a separations instrument comprising a column chromatography device and at least one component selected from a detecting means, an introducing means, or an accepting means. The column chromatography device may comprise a nanocolumn having a cylindrical interior for accepting a stationary phase, a particulate stationary phase material packed within the nanocolumn. The in situ frit is within the nanocolumn, and adjacent to and integral with the stationary phase material. The in situ frit also comprises an intimate mixture of particles of a stationary phase material and a polymeric network of cross-linked poly(diorganosiloxane) and particles of stationary phase material suspended in the network. The detecting means is operatively connected to the nanocolumn and is capable of measuring physicochemical properties (light absorption/emission, conductivity, etc.). The introducing means is operatively connected to the nanocolumn and is capable of conducting a liquid into the nanocolumn. The accepting means is capable of holding the nanocolumn in a configuration in which the nanocolumn is operatively connected to either a detecting means or an introducing means.

Furthermore, the invention relates to a chromatography device prepared by the steps of providing a nanocolumn having a cylindrical interior for accepting a stationary phase, and forming a stationary phase within the nanocolumn. Such a stationary phase may comprise a particulate stationary phase material, and an in situ frit adjacent to and integral with the stationary phase material, wherein the in situ frit comprises an intimate mixture of particles of a stationary phase material and a polymeric network of cross-linked poly(diorganosiloxane) and the particles are suspended in the network.

Furthermore, the invention relates to a method of making a chromatography device comprising the steps of providing a nanocolumn having a cylindrical interior for accepting a stationary phase, and forming a stationary phase within the nanocolumn. The stationary phase comprises a particulate stationary phase material, and an in situ frit adjacent to and integral with the stationary phase material. Generally, the in situ frit comprises an intimate mixture of particles of a stationary phase material and a polymeric network of cross-linked poly(diorganosiloxane), and wherein the particles are suspended in the network.

In one aspect, the step of "forming a stationary phase" may comprise the steps of preparing a mixture of the stationary phase material, a solvent, and synthetic precursors of cross-linked poly(diorganosiloxane); introducing this mixture into an end of the nanocolumn; allowing the solvent to evaporate at room temperature; curing the dried mixture. Curing may be achieved by heating the nanocolumn and the mixture therein to a temperature of between about 70° C. to about 150° C. for a period of time ranging from about 0.5 hours to about 3 hours to thereby produce an in situ frit. Optionally, the in situ frit may be sintered by heating the nanocolumn and the in situ frit therein to a temperature of between about 250° C. and about 350° C. for a period of time ranging from about 5 seconds to about 30 second.

Likewise, the invention discloses a method of making a chromatography device comprising the steps of preparing a mixture of a stationary phase material, a solvent, and polymer reagents that produce cross-linked poly(diorganosiloxane); introducing this mixture into an end of the nanocolumn; allowing the solvent to evaporate at room temperature; and curing the dried mixture. Such a curing step may include heating the nanocolumn and the mixture therein to a temperature of between about 70° C. to about 150° C. for a period of time ranging from about 0.5 hours to about 3 hours to thereby produce an in situ frit. Also, the method may include a step of optionally sintering the in situ frit by heating the nanocolumn and the in situ frit therein to a temperature of between about 250° C. and about 350° C. for a period of time ranging from about 5 seconds to about 30 second.

The present invention also relates to methods of using the chromatography devices and materials described herein. For example, the invention pertains to an analytical method of separating components of a mixture comprising a step of contacting the mixture with a column chromatography device of the invention. Similarly, the invention also covers a separations instrument comprising a column chromatography device of the invention. Additionally, the inventions discloses methods of analyzing components of a mixture comprising a step of contacting such a mixture with a column chromatography device of the invention, as well as methods of separating components of a mixture comprising a step of contacting such a mixture with a column chromatography device of the invention.

Furthermore, the instant application pertains to a separations instrument comprising a column chromatography device of the invention, such as a CE, nanoLC, or CEC instrument. Such instruments may comprise a pumping means for moving liquid through the column chromatography device, and a detecting means for analyzing the column chromatography device effluent.

DETAILED DESCRIPTION OF THE INVENTION

Figure 1A:
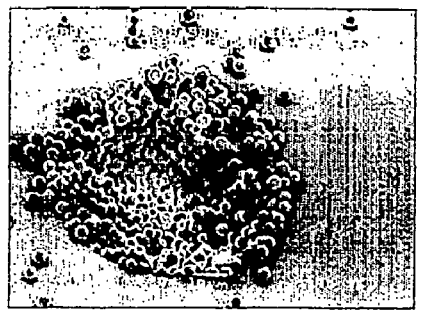
FIG. 1 shows SEM images of frits according to Example 1 formed with (A) 1% PDMS, (B) 5% PDMS, and (C) 10% PDMS solutions in 1,4-dioxane.

For convenience, some definitions of terms referred to herein are set forth below.

The term "stationary phase material" or "packing material" means a loose particulate material intended for chromatographic use. Once the material is packed and in contact with the mobile phase, it typically is referred to as the "stationary phase," i.e., one of the two chromatographic phases. That is, the stationary phase usually consists of a specific stationary phase material, which has been "packed" into a column. The expression "chromatographic bed," "packed bed," or simply "bed" may be used as a general term to denote any of the different forms in which the stationary phase is used. The stationary phase is the part of a chromatographic system responsible for the retention of the analytes, which are being carried through the system by the mobile phase. The "packing" is the active solid, stationary phase plus any solid support that is contained in the chromatographic column. A "solid support" is a solid that holds or retains the stationary phase but typically does not substantially contribute to the separation process. An inlet or outlet frit in a typical liquid chromatography column is an example of a solid support. Therefore, an in situ frit according to the present invention is a solid support, a component of the packing (because it is part stationary phase material), and a component of the stationary phase (at least to the extent that the stationary phase material within the frit contributes to the separation process.) An "immobilized stationary phase" is a stationary phase in which the stationary phase material that has been packed in a chromatographic column and has been immobilized, e.g., by either a physical attraction, chemical bonding, or by in situ polymerization. IUPAC, *Pure and Applied Chemistry* 69, 1475-1480 (1997).

"Alkyl-bonded" stationary phase or material is a bonded stationary phase (or material) in which the group bound to the surface contains an alkyl chain (usually between $C_1$ and $C_{18}$). "Phenyl-bonded" stationary phase (or material) is a bonded stationary phase (or material) in which the group bound to the surface contains a phenyl group. "Cyano-bonded" stationary phase (or material) is a bonded stationary phase in which the group bound to the surface contains a cyanoalkyl group (e.g. —$(CH_2)_n$—CN). "Diol-bonded" stationary phase (or material) is a bonded stationary phase in which the group bound to the surface contains a vicinal dihydroxyalkyl group (e.g., —$(CH_2)$n-CHOH—$CH_2OH$). "Amino-bonded" stationary phase (or material) is a bonded stationary phase in which the group bound to the surface contains an aminoalkyl group (e.g., —$(CH_2)_n$—$NH_2$). "Capped" stationary phase (or material) (also known as "end-capped" stationary phase or material) is a bonded stationary phase (or material) that has been treated with a second (usually less bulky) reagent, which is intended to react with remaining functional (e.g., silanol) groups which have not been substituted by the original reagent because of steric hindrance.

According to the present invention, the term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

Alkyl groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or cycloalkyl or alicyclic groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups).

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain), and more preferably 4 or fewer. Likewise, preferred cycloalkyl groups have from 3-8 carbon atoms in their ring structure, and more preferably have 5 or 6 carbons in the ring structure. The term "$C_1$-$C_6$" includes alkyl groups containing 1 to 6 carbon atoms.

Moreover, unless otherwise specified the term alkyl includes both "unsubstituted alkyls" and "substituted alkyls," the latter of which refers to alkyl moieties having substituents replacing one or more hydrogens on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or aromatic or heteroaromatic moieties.

An "arylalkyl" moiety is an alkyl group substituted with an aryl (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent moiety derived from the corresponding alkyl group. The terms "alkenyl" and "alkynyl" refer to unsaturated aliphatic groups analogous to alkyls, but which contain at least one double or triple carbon-carbon bond respectively. Suitable alkenyl and alkynyl groups include groups having 2 to about 12 carbon atoms, preferably from 1 to about 6 carbon atoms. A "vinyl" group is an ethylenyl group (i.e., —CH=CH$_2$). A "styryl" group is a vinyl-substituted phenyl group.

The term "aromatic group" includes unsaturated cyclic hydrocarbons containing one or more rings. Aryl groups can also be fused or bridged with alicyclic or heterocyclic rings which are not aromatic so as to form a polycycle (e.g. tetralin). The term "aromatic group" includes unsaturated cyclic hydrocarbons containing one or more rings. In general, the term "aryl" includes groups, including 5- and 6-membered single-ring aromatic groups that may include from zero to four heteroatoms, for example, groups derived from benzene, pyrrole, furan, thiophene, thiazole, isothiaozole, imidazole, triazole, tetrazole, pyrazole, oxazole, isooxazole, pyridine, pyrazine, pyridazine, and pyrimidine, and the like. An "arylene" group is a divalent moiety derived from an aryl group. The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms The term "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The term "nitro" means —NO$_2$; the term "halogen" or "halo" designates —F, —Cl, —Br or —I; the term "thiol," "thio," or "mercapto" means SH; and the term "hydroxyl" or "hydroxyl" means —OH.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen) which allow the molecule to perform its intended function. Examples of substituents include moieties selected from straight or branched alkyl (preferably C$_1$-C$_5$), cycloalkyl (preferably C$_3$-C$_8$), alkoxy (preferably C$_1$-C$_6$), thioalkyl (preferably C$_1$-C$_6$), alkenyl (preferably C$_2$-C$_6$), alkynyl (preferably C$_2$-C$_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, (CR'R")$_{0-3}$NR'R" (e.g., —NH$_2$), (CR'R")$_{0-3}$CN (e.g., —CN), NO$_2$, halogen (e.g., F, Cl, Br, or I), (CR'R")$_{0-3}$C(halogen)$_3$ (e.g. —CF$_3$), (CR'R")$_{0-3}$CH(halogen)$_2$, (CR'R")$_{0-3}$CH$_2$(halogen), (CR'R")$_{0-3}$CONR'R", (CR'R")$_{0-3}$(CNH)NR'R", (CR'R")$_{0-3}$S(O)$_{1-2}$NR'R", (CR'R")$_{0-3}$CHO, (CR'R")$_{0-3}$O(CR'R")$_{0-3}$H, (CR'R")$_{0-3}$S(O)$_{0-3}$R' (e.g., —SO$_3$H), (CR'R")$_{0-3}$O(CR'R")$_{0-3}$H (e.g., —CH$_2$OCH$_3$ and —OCH$_3$), (CR'R")$_{0-3}$S(CR'R")$_{0-3}$H (e.g., —SH and —SCH$_3$), (CR'R")$_{0-3}$OH (e.g., —OH), (CR'R")$_{0-3}$COR', (CR'R")$_{0-3}$(substituted or unsubstituted phenyl), (CR'R")$_{0-3}$(C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a C$_1$-C$_5$ alkyl, C$_2$-C$_5$ alkenyl, C$_2$-C$_5$ alkynyl, or aryl group, or R' and R" taken together are a benzylidene group or a —(CH$_2$)$_2$O(CH$_2$)$_2$— group.

A "substituent" as used herein may also be, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety.

The present invention provides improved nanocolumn chromatography devices. A "nanocolmn" may be a capillary columns (i.e., <100 μm, typically 50-75 μm), such as those known in the art for use in CE, nanoLC, and CEC. Such capillary columns are preferred because the in situ frits of the invention formed therein are better able to withstand high chromatography pressures (because of the smaller cross-sectional surface area). Also, when capillary columns are heated, e.g., when the material therein is sintered, they are better able to dissipate heat. A capillary chromatography column generally comprises a fused silica capillary tube, which may be circular in cross-section, and which may be coated with another material, e.g., polyimide.

In the devices of the invention, a portion of the nanocolumn (or capillary column) is packed with a particulate stationary phase material (e.g., bonded silica particles having a diameter of about 1 to 3 µm). The term "column" as used herein may refer to the solid cylindrical container, e.g., a hollow fused silica capillary, or the term may refer to the packed bed of stationary phase material within the cylindrical container, or the term may refer to both aspects. A nanocolumn may be made of made of fused silica, glass, stainless steel, a polymer, a ceramic, or a mixture thereof. One particular aspect of the invention refers to fused silica columns, particularly those coated with polyimide. Also, a nanocolumn used in the invention has a cylindrical interior for accepting a stationary phase. The inner diameter of such a nanocolumn is about 10 µm to about 1.0 mm. In another embodiment, the inner diameter is about 25 µM to about 320 µm or even about 500 µm. Packed columns of the invention may be of a variety of lengths depending on the intended application, however, an exemplary length is approximately 20 cm.

An exemplary chromatography device of the invention therefore includes a nanocolumn, e.g., a capillary, packed with a particulate stationary phase material and a solid support. The solid support, which may be referred to as an "in situ frit" is adjacent to and integral with the stationary phase material.

A wide variety of particulate stationary phase materials may be used in the invention. Accordingly, the stationary phase or packing of a chromatography devices of the invention is made from a "particulate stationary phase material" or "particles of a stationary phase material." Furthermore, the stationary phase retains a particulate nature, as opposed to being a monolith material. Monolith materials are described, for example, in international PCT application no. PCT/US02/25,193.

By way of example, the particles of the stationary phase material may have an average size/diameter of about 0.5 µm to about 10.0 µm, or more particularly about 3 µm to about 5.0 µm. In certain circumstances, particle size distribution should be within 10% of the mean. Typically, the stationary phase material is porous, although it may also be non-porous. Additionally, the stationary phase material may have an average pore diameter of about 70 Å to about 300 Å; or a specific surface area of about 50 m$^2$/g to about 250 m$^2$/g; or a specific pore volume of about 0.2 to 1.5 cm$^3$/g. Although it should be noted that chemical modification of the adsorbent surface may have an influence on the surface area and the pore volume of the stationary phase material. This effect is significant in the case of, e.g., bonded silica, which may have surface area of 350 m$^2$/g reduced to 170 m$^2$/g after bonding with octadecylsilane.

Generally, it will be preferable to use spherically shaped particles rather than irregularly shaped particles. It is well known in the art that irregularly-shaped materials are often more difficult to pack than spherical materials. It is also known that spherical materials are easier to pack and exhibit greater packed bed stability than columns packed with irregularly-shaped materials of the same size.

In general, any particulate stationary phase material known in the art for use in HPLC columns may also be used in the chromatography devices of the present intention. Examples of suitable particulate stationary phase materials for use include alumina, silica, titanium oxide, zirconium oxide, a ceramic material, an organic polymer, or a mixture thereof. Preferred stationary phase materials have been bonded with a surface modifier. Such surface modifiers may be an alkyl group, alkenyl group, alkynyl group, aryl group, cyano group, amino group, diol group, nitro group, ester group, or an alkyl or aryl group containing an embedded polar functionality. For example, an alkyl group surface modifier group may be a methyl, ethyl, propyl, isopropyl, butyl, tert-butyl, sec-butyl, pentyl, isopentyl, hexyl, cyclohexyl, octyl, or octadecyl group. Further examples of fitting particulate stationary phase materials include alkyl-bonded, phenyl-bonded, cyano-bonded, diol-bonded, and amino-bonded silica, and mixtures thereof. Suitable materials are readily available from a variety of commercial sources, including Waters Chromatography (Milford, Mass., USA), Alltech Associates, Inc. (Deerfield, Ill., USA), Beckman Instruments, Inc. (Fullerton, Calif., USA), Gilson, Inc. (Middleton, Wis., USA), EM Science (Gibbstown, N.J., USA), Supelco, Inc. (Bellefonte, Pa., USA).

Still further examples of stationary phase materials that may be used in the present invention include porous inorganic/organic hybrid particles, as described, for example, in international PCT application nos. PCT/US02/25,250 and PCT/US00/03,052 (WO 2000/45,951). "Hybrid", i.e., as in "porous inorganic/organic hybrid particles" includes inorganic-based structures wherein an organic functionality is integral to both the internal or "skeletal" inorganic structure as well as the hybrid material surface. The inorganic portion of the hybrid material may be, e.g., alumina, silica, titanium or zirconium oxides, or ceramic material. In a preferred embodiment, the inorganic portion of the hybrid material is silica. In a preferred embodiment where the inorganic portion is silica, "hybrid silica" refers to a material having the formula $SiO_2/(R^2_pR^4_qSiO_t)_n$ or $SiO_2/[R^6(R^2_rSiO_t)_m]_n$ wherein $R^2$ and $R^4$ are independently $C_1$-$C_{18}$ aliphatic styryl, vinyl, propanol, or aromatic moieties (which may additionally be substituted with alkyl, aryl, cyano, amino, hydroxyl, diol, nitro, ester, ion exchange or embedded polar functionalities), $R^6$ is a substituted or unsubstituted $C_1$-$C_{18}$ alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, more preferably, 0.1 to 1, and even more preferably 0.2 to 0.5. $R^2$ may be additionally substituted with a functionalizing group R. The term "functionalizing group" includes organic groups which impart a certain chromatographic functionality to a chromatographic stationary phase, including, e.g., octadecyl ($C_{18}$) or phenyl. Such functionalizing groups are present in, e.g., surface modifiers such as disclosed herein which are attached to the base material, e.g., via derivatization or coating and later cross-linking, imparting the chemical character of the surface modifier to the base material. In an embodiment, such surface modifiers have the formula $Z_a(R')_bSi$—R, where Z=Cl, Br, I, $C_1$-$C_5$ alkoxy, dialkylamino, e.g., dimethylamino or trifluoromethanesulfonate; a and b are each an integer from 0 to 3 provided that a+b=3; R' is a $C_1$-$C_6$ straight, cyclic or branched alkyl group, and R is a functionalizing group. Likewise, R' may be, e.g., methyl, ethyl, propyl, isopropyl, butyl, tert-butyl, sec-butyl, pentyl, isopentyl, hexyl or cyclohexyl; preferably, R' is methyl.

An "in situ frit" of the invention may be a mixture of the stationary phase material and a polymeric network of cross-linked poly(diorganosiloxane), e.g., poly(dimethylsiloxane). In certain embodiments, particularly when larger diameter nanocolumns are used, the in situ frit may optionally be sintered.

In general, an in situ frit of the invention may be made my placing a mixture of a stationary phase material, a solvent, and polymer reagents into an end of a nanocolumn (having a cylindrical interior for accepting the stationary phase). The polymer reagents are compounds that produce cross-linked poly(diorganosiloxane) after "curing." The mixture in the nanocolumn is maintained at room temperature or warmer in order remove solvent by evaporation. The nanocolumn may then be further heated to promote curing, or it may be sintered at a higher temperature.

The resulting material within the column is a suspension of discrete particles, which may be visually identified by microscopy, in a polymeric network. As the poly(diorganosiloxane) cures, it reacts with itself and the other polymer reagents to form cross-links which all together form a network or matrix throughout the particulate solid phase material. Such a mixture is therefore an "intimate" homogenous mixture, as opposed to a simple mixture of two separate components having no interaction with each other. As such, the initial product is an immobilized stationary phase, rather than a monolith. An in situ frit thus prepared may then be sintered which thereby causes further structural changes that make the frit stronger.

The poly(diorganosiloxane) polymers used in the present invention typically include those formed from precursors including the chlorosilanes such as methylchlorosilanes, ethylchlorosilanes, and phenylchlorosilanes, and the like. The poly(diorganosiloxane) polymers may also be cross-linked when a branched polymerizable monomer is included in the polymer and subsequently reacted. The polymer reagents used in the instant invention may themselves also be polymers. A particularly preferred polymer is poly(dimethylsiloxane) ("PDMS"). See, e.g., U.S. Pat. Nos. 4,374,967, 4,529,789, 4,831,070, 4,882,377, 6,169,155, and 5,571,853.

Although the polymers described herein are referred to as "poly(dimethylsiloxane)," etc., one skilled in the art will appreciate that such polymers may contain amounts of other units, including, e.g., monomethylsiloxane and other mono- or diorganosiloxane units, which are often formed during synthesis of the polymer, so long as these units do not substantially alter the properties.

The poly(diorganosiloxane) of the invention may be a polymer having a repeat unit of the formula —($-R^1R^2SiO-$)—, wherein $R^1$ and $R^2$ are independently hydrogen, a $C_1$-$C_{18}$ aliphatic group, an aromatic group, or a cross-linking group. Alternatively, the poly(diorganosiloxane) may be a polymer having the formula ($-R^1R^2SiO-$)$_n$, wherein $R^1$ and $R^2$ are independently hydrogen, a $C_1$-$C_{18}$ aliphatic group, an aromatic group, or a cross-linking group, and n represents the number of repeat units. For example, $R^1$ and $R^2$ may each be a straight or branched-chain alkyl or cycloalkyl group, such as a $C_1$-$C_6$ alkyl group, including methyl, ethyl, n-propyl, isopropyl, butyl, sec-butyl, and tert-butyl groups.

Cross-linked PDMS (or "siloxane") may be made from a variety of "polymer reagents," for example, a polyorganosiloxane that is cured with an organohydrogensiloxane cross-linking reagent. As used herein, the term "cross-linking" group is a hydrocarbon group containing a polymerizable alkenyl group, although the term "cross-linking group" may also refer to the product of the polymerization of such a group. Examples of cross-linking groups include a vinyl group or a styryl group. For example, in the presence of a suitable catalyst (e.g., a platinum compound), a vinyl group of a cross-linkable polymer reagent may react with another polymer reagent (e.g., an organohyrogensiloxane) containing an S—H bond to thereby cross-link the material. The polymer reagents used in the invention may also include a poly(dimethylsiloxane) that does not have cross-linkable groups. These "non-functional" polymers do not substantially undergo a cross-linking reaction, and examples include polymers of the general formula HO[Si(CH$_3$)$_2$O]$_m$H, where m has an average value of about 50 to about 1000.

Generally, one of the polymer reagents used in the invention contains a vinyl group on a polyorganosiloxane, which will react with a suitable cross-linker. A suitable cross-linker is an organohydrogensiloxane having a Si—H bond, generally with an average of more than one Si—H bond per molecule and no more than one Si—H bond per silicon atom. The other substituents on the silicon atom may be, e.g., lower alkyl groups. An example of an organohydrogensiloxane compound which can be employed in the practice of the present invention is 1,3,5,7-tetramethylcyclotetrasiloxane (or tetramethyl tetravinyl cyclotetrasiloxane). Another cross-linker is a dimethylhydrogensiloxane-terminated polydimethylsiloxane, HMe$_2$Si(OMe$_2$Si)$_x$H. Further examples of cross-linking polymer reagents comprise a polymer of dimethylsiloxane units, methylhydrogensiloxane units, and trimethylsiloxane units.

Accordingly, the polymer reagents used in the invention typically comprise at least four components: (1) an organopolysiloxane containing a silicon-bonded alkenyl group, (2) a non-functional organopolysiloxane, (3) an organohydrogenpolysiloxane, and (4) a catalyst.

In one aspect of the invention, the poly(diorganosiloxane) is selected from poly(dimethylsiloxane) polymers. Likewise, the cross-linked poly(diorganosiloxane) is selected from the group consisting of cross-linked poly(dimethylsiloxane) polymers.

For example, a cross-linkable polymer reagent may contain an average of at least two silicon-bonded alkenyl groups per molecule. Suitable alkenyl groups contain from 2 to about 6 carbon atoms, such as vinyl, allyl, butenyl (e.g., 1-butenyl), and hexenyl (e.g., 1-hexenyl) groups. The alkenyl groups may be located at terminal, pendant (non-terminal), or both terminal and pendant positions. The remaining silicon-bonded organic groups may be monovalent hydrocarbon and monovalent halogenated hydrocarbon groups free of aliphatic unsaturation (e.g., alkyl groups, particularly lower alkyl groups, such as methyl, ethyl, propyl, and butyl) as well as aryl groups such as phenyl; and halogenated alkyl groups such as 3,3,3-trifluoropropyl. A cross-linkable polymer reagent may be linear, or it may contain branching because of trifunctional siloxane units. Examples of poly(diorganosiloxane) reagents may have the general formula $R^4R^3_2SiO(R^3_2SiO)_nSiR^3_2R^4$ wherein each $R^3$ is independently an alkyl group or halogenated hydrocarbon groups free of aliphatic unsaturation (e.g., alkyl or aryl group); $R^4$ is an alkenyl group; and n has a value such that the viscosity is convenient. Typically, n is from about 200 to about 600. Preferably, $R^3$ is methyl and $R^4$ is vinyl.

For example, a cross-linkable polymer reagents, particularly poly(diorganosiloxane) compounds, useful in the invention include the following:

(H$_2$C=CH)Me$_2$SiO(Me$_2$SiO)$_n$SiMe$_2$(CH=CH$_2$), (H$_2$C=CH)Me$_2$SiO(Me$_2$SiO)$_x$(MePhSiO)$_y$SiMe$_2$(CH=CH$_2$), (H$_2$C=CH)Me$_2$SiO(Me$_2$SiO)$_x$(Me(CH=CH$_2$)SiO)$_y$SiMe$_2$(CH=CH$_2$), (H$_2$C=CH)MePhSiO(Me(CH=CH$_2$)SiO)$_x$(MePhSiO)$_y$SiMePh(CH=CH$_2$),

Me$_3$SiO(Me$_2$SiO)$_x$(Me(CH=CH$_2$)SiO)$_y$SiMe$_3$,

PhMe(H$_2$C=CH)SiO(Me$_2$SiO)$_n$SiPhMe(CH=CH$_2$), and so on, where x+y=n, and n is about 100 to 1000. Preferred poly(diorganosiloxane) polymer reagents include dimethylvinylsiloxy-terminated polydimethylsiloxanes.

Examples of organohydrogensiloxane polymer reagents include having the formula $R^7Si(OSiR^8_2H)_3$ wherein $R^7$ is a branched or unbranched allyl group having 1 to 18 carbon atoms or an aryl group, and $R^8$ is a branched or unbranched alkyl group having 1 to 4 carbon atoms. Examples of suitable R7 groups include methyl, ethyl, n-propyl, isopropyl, butyl, 2-methylpropyl, pentyl, 2-methylbutyl, 2,2-dimethylpropyl, hexyl, 2-methylpentyl, 3-methylpentyl, 2,2-dimethybutyl, 2,3-dimethylbutyl, heptyl, 2-methyhexyl, 3-methylhexyl, 2,2-dimethylpentyl, 2,3-dimethylpentyl, 2,4-dimethylpentyl, 3,3-dimethylpentyl, 3-ethylpentyl, 2,2,3-trimethylbutyl, octyl, nonyl, decyl, undecyl, dodecyl, tridecyl, tetradecyl, pentadecyl, hexadecyl, heptadecyl, and octadecyl, phenyl, tolyl, and benzyl. Preferably $R^7$ is n-propyl. Examples of suitable $R^8$ groups include methyl, ethyl, propyl, n-butyl, and 2-methylpropyl.

In general, the dimethyl siloxane or methylhydrogen siloxane may have an average molecular weight of about 10 Da to about 10,000, or more particularly average molecular weight of about 100 Da to about 1,000. Similarly, the vinyl-substituted dimethyl siloxane may have an average molecular weight of about 500 Da to about 100,000 Da, or more particularly an average molecular weight of about 10,000 Da to about 40,000 Da.

The polymer reagents are reacted, i.e., cross-linked or "cured," in situ by heating. The in situ frit produced thereby may be further immobilized by sintering. In one embodiment, the curing step comprises heating the mixture to a temperature of between about 25° C. and about 150° C. for a period of time ranging from about 1 hour to about 48 hours.

The curing step may be facilitated by addition of a small amount of a platinum hydrosilation catalyst, e.g., a platinum catalyst that catalyzes the reaction between silicon-bonded hydrogen and vinyl groups. More generally, the hydrosilylation catalyst may be any active transition metal catalyst as known in the art, particularly those comprising rhodium, ruthenium, palladium, osmium, or iridium, in addition to platinum. Suitable catalysts include chloroplatinic acid catalyst, U.S. Pat. No. 2,823,218, and the reaction products of chloroplatinic acid and an organosilicon compound, see, e.g., U.S. Pat. No. 3,419,593. Also applicable are the platinum hydrocarbon complexes described in U.S. Pat. Nos. 3,159,601 and 3,159,662, and the platinum acetyl acetonate shown in U.S. Pat. No. 3,723,497, and the platinum alcoholate catalysts described in U.S. Pat. No. 3,220,972. For any of the particular platinum catalysts selected, the practitioner will be able to determine an optimum catalytically effective amount to promote curing. Platinum catalysts have been used effectively in amounts sufficient to provide from about 0.1 to 40 parts by weight of platinum per million parts by weight of total formulation.

The catalyst may be any catalyst that can promote the addition reaction between an alkenyl group and a Si—H group. The platinum group metal catalysts include, for example, chloroplatinic acid, alcohol-modified chloroplatinic acids, coordination compounds of chloroplatinic acid with an olefin, vinylsiloxane or acetylene compound, tetrakis-(triphenylphosphine)palladium, chlorotris(triphenylphosphine)rhodium and the like, among which particularly preferred are platinum compounds.

In the composition of the present invention, the catalyst is normally present in an amount of from 0.1 to 100 ppm based on the total amount of the other components although a determination of the appropriate amount for a particular situation will be within the scope of routine experimentation typically undertaken by the skilled practitioner.

The poly(diorganosiloxane) polymers used in the present invention typically include those formed from precursors including the chlorosilanes such as methylchlorosilanes, ethylchlorosilanes, and phenylchlorosilanes, and the like. The poly(diorganosiloxane) polymers may also be cross-linked when a branched polymerizable monomer is included in the polymer and subsequently reacted.

A variety of known additives may be included in the polymer reagents. For example, inorganic fillers such as finned silica, silica aerogel, precipitates silica, ground silica, and the like may be added in order to modulate the physical properties of the polymeric network, e.g., hardness, mechanical strength, etc. Certain controlling agents such as cyclic polymethylvinylsiloxane compounds, acetylene compounds, organophosphorus compounds, and the like can be added to the composition, thereby controlling the rate of the curing reaction. Although such additives may be added to impart additional desirable features, additives preferably do not substantially reduce the chromatographic efficiency or usefulness of the resulting materials.

Therefore, in yet another example, the cross-linked poly(diorganosiloxane) polymers of the invention may be made from polymer reagents contributing the following exemplary units: One unit may be primarily comprised of dimethylsiloxane ($Me_2SiO$) repeat units, which may be 80 to 96.5 mol % of the total siloxane units in the polymer. A second unit of the polyorganosiloxane may be monomethylsiloxane ($MeSiO_{1.5}$), which may be 2 to 10.0 mol % of the total siloxane units in the polymer. The $MeSiO_{1.5}$ group imparts a higher melting temperature than without monomethylsiloxane units (a polymer chain only of dimethylsiloxane units would crystallize at approximately −40° C., whereas monomethylsiloxane units randomly placed along the siloxane polymer chain avoids the crystalline phase). A third unit may be the trimethylsiloxane unit ($Me_3SiO_{0.5}$), which functions as an endblocker for the polymer chain, and may be 1.25 to 6.0 mol % of the total organosiloxane. A final unit in the siloxane polymer may be a vinyl-containing siloxane unit, e.g., dimethylvinylsiloxane ($Me_2(H_2C=CH)SiO_{0.5}$), where the vinyl group is in a terminal position (a terminal vinyl group cures more quickly than an internal vinyl group (i.e., $Me(H_2C=CH)SiO$)). The terminal vinyl unit also functions as an endblocker in conjunction with the trimethylsiloxane units, and it may be 0.25 to 4 mol % of the total organosiloxane units in the polymer.

In another example, the cross-linked poly(diorganosiloxane) is produced by the reaction of a polymer reagent comprising vinyl-substituted dimethyl siloxane, such as dimethylvinyl-terminated dimethyl siloxane. Other specific examples of polymer reagents include dimethyl siloxane, methylhydrogen siloxane, dimethylvinylated silica, trimethylated silica, tetramethyl tetravinyl cyclotetrasiloxane, and tetra(trimethylsiloxy) silane.

Exemplary poly(dimethylsiloxane) polymers include those sold under the tradename Sylgard by the Dow Corning Corporation (Midland, Mich., USA). The PDMS polymer may easily be produced by mixing the precursor and the catalyst of a commercially available Sylgard kit in an appropriate ratio followed by curing. Sylgard poly(dimethylsiloxane) polymers may be readily synthesized by curing a mixture of A and B components, where A is, e.g., dimethylvinyl terminated polydimethyl siloxane and B is, e.g., trimethyl terminated siloxane with partially hydrogen-substituted methyl side groups. Polymers having various properties may be synthesized simply by varying the weight ratio of A to B, and the molecular weight and functionality of the A and B kit components. For example, in the product known by the tradename Dow Sylgard 527, the average molecular weight distribution of both A and B components is broad and centers around 20,000 grams/mole, and the functionality of the B component is about 102.

Generally, a Sylgard kit allows facile synthesis of PDMS polymer. Sylgard poly(dimethylsiloxane) polymers may be readily synthesized by curing a mixture of A and B components, where A is, e.g., dimethylvinyl terminated polydimethyl siloxane and B is, e.g., trimethyl terminated siloxane with partially hydrogen-substituted methyl side groups. Polymers having various properties may be synthesized simply by varying the weight ratio of A to B, and the molecular weight and functionality of the A and B kit components.

More generally, poly(diorganosiloxane) polymers of the present invention may be prepared from a vinyl endblocked poly(diorganosiloxane), e.g., poly(dimethylsiloxane), component "A", and another organosiloxane, component "B", optionally with a catalyst. Different polymers may be similarly synthesized by varying the compositions of A and B, as well as the relative amounts of the A and B components. The triorganosiloxy endblocked poly(dimethylsiloxane) is referred to as "A." The triorganosiloxy group may contain a vinyl radical and two methyl radicals bonded to silicon or a vinyl, a phenyl, and a methyl radical bonded to silicon. For examples, A may have the following chemical structure:

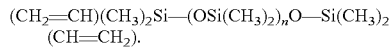
$(CH_2=CH)(CH_3)_2Si—(OSi(CH_3)_2)_nO—Si(CH_3)_2(CH=CH_2)$.

Component A may be any triorganosiloxy endblocked poly (dimethylsiloxane) that exhibits a suitable chromatographic properties in the chromatographic columns and methods of the invention. The dispersity index value takes into account the concentration of all polymeric species present in A, and is obtained by dividing the weight average molecular weight of a given polymer by its number average molecular weight. Two or more poly(dimethylsiloxane) polymers of different molecular weights may be mixed to achieve a different dispersity index and molecular weight distribution. Another method of preparing preferred embodiments of A is described, e.g., in U.S. Pat. No. 3,445,426. Preferably, the triorganosiloxy endblocking group of A is a dimethylvinylsiloxy group.

The organosiloxane copolymer "B" may be a trimethyl terminated siloxane with partially hydrogen-substituted methyl side groups. These polymers may contain units of the formulae $(CH_3)_2(CH_2=CH)SiO_{1/2}$, $(CH_3)_3SiO_{1/2}$, and $SiO_2$. U.S. Pat. No. 2,676,182. These copolymers contain certain percentages by weight of hydroxyl groups, which may changed by altering the concentration of triorganosiloxane capping agent. For example, a silica hydrosol may be reacted with hexamethyldisiloxane or trimethylchlorosilane under acidic conditions, followed by reaction with silazane, siloxane, or silane containing a vinyl and two methyl radicals bonded to silicon.

The A and B components react in the presence of a suitable catalyst to yield an elastomeric gel. A preferred class of catalysts includes the platinum compositions that are known to catalyze the reaction between silicon-bonded hydrogen atoms and olefinic double bonds, particularly silicon-bonded vinyl groups, and that are soluble in A. A particularly suitable class of platinum-containing catalysts are the complexes prepared from chloroplatinic acid and certain unsaturated organosilicon compounds and described in U.S. Pat. No. 3,419,593. The platinum catalyst may be present in an amount sufficient to provide at least one part by weight of platinum for every one million parts by weight of A, however it is preferable to use as little catalyst as possible. Mixtures containing components A and B with a platinum catalyst may begin to cure immediately on mixing at room temperature, and therefore it may be preferable to use a catalyst inhibitor, such as those inhibitors described in U.S. Pat. No. 3,445,420, including inhibitors such as acetylenic alcohols, particularly 2-methyl-3-butyn-2-ol. Once the curing reaction commences, however, it proceeds at the same rate as if no inhibitor were present. Inhibited compositions are typically cured by heating them to a temperature of about 70° C. or higher. If a catalyst is used, particularly catalysts such as platinum catalysts that are active at very low concentrations, then care must be taken to completely remove all traces of catalyst from the ultimate chromatography column. Residual catalyst may lead to the catalysis of reactions with of analytical compounds as they pass through a contaminated stationary phase material in a chromatography column, and therefore compromise the usefulness of the material. In the case of Sylgard 184, the manufacturer recommends that it be cured using for 24 hours at 23° C., or 4 hours at 65° C., or 1 hour at 100° C., or 15 minutes at 150° C.; although large amounts may require longer times in order to reach the curing temperature. At 23° C. the material will have cured sufficiently in 24 hours to be handled; however full mechanical and electrical properties will only be fully achieved after 7 days.

Accordingly, the present invention is directed to an in situ frit for immobilizing a stationary phase material in a chromatography nanocolumn comprising an intimate mixture of particles of a stationary phase material and a polymeric network of cross-linked poly(diorganosiloxane), wherein the particles are suspended in the network.

Likewise, the invention relates to a medium for molecular separations comprising a particulate stationary phase material, and an in situ frit adjacent to and integral with the stationary phase material. The in situ frit comprises an intimate mixture of particles of a stationary phase material and a polymeric network of cross-linked poly(diorganosiloxane), and the particles are suspended in the network.

In a further embodiment, the invention relates to a column chromatography device comprising a nanocolumn having a cylindrical interior for accepting a stationary phase, a particulate stationary phase material packed within the nanocolumn, and an in situ frit within the nanocolumn, and adjacent to and integral with the stationary phase material. The in situ frit comprises an intimate mixture of particles of a stationary phase material and a polymeric network of cross-linked poly (diorganosiloxane), and the particles are suspended in the network.

In order to maximize the usefulness of the column chromatography devices of the invention, the relative amount of the polymer component to the stationary phase material should be sufficiently high to satisfactorily immobilize the stationary phase. On the other hand, the relative amount of polymer component should low enough that it does not substantially alter the chromatographic partitioning properties of the solid phase material itself. Indeed, if the relative amount of the polymeric component is too high, then the resulting back pressure may be impracticably high. Although the optimal relative amount of polymer to stationary phase material will depend on the precise circumstances, one skilled in the art will be able to ascertain with no more than routine experimentation an appropriate composition in accord with the objects of the present invention. By way of example, the intimate mixture of particles (of stationary phase material) and a polymeric network (of cross-linked poly(diorganosiloxane)) as described herein may be approximately a 10:1 (w/w) composition, or a 15:1 (w/w) composition, or even a 20:1 (w/w) composition, or even a 25:1 (w/w) composition. In some cases, the intimate mixture may even be approximately a 50:1 (w/w) composition of particles:polymeric network, or even a 70:1 (w/w) composition, or a 100:1 (w/w) composition, or even a 1000:1 (w/w) composition. Such relative amounts may be achieved by calculating or estimating the stoicheometric equivalents of each reagent or component that is to be included in the manufacture of the materials. Likewise, such ratios may be determined by post facto empirical analysis of the resulting products, e.g., by combustion analysis or other such methods.

The invention also pertains to a separations instrument comprising a column chromatography device and at least one component selected from a detecting means, an introducing means, or an accepting means. One skilled in the art will appreciate that a variety of detecting means, introducing means, and accepting means may be used according to the invention in analogous manner as the equivalent or even identical equipment is used in, e.g., HPLC and other common analytical chromatography methods. The column chromatography device may comprise a nanocolumn having a cylindrical interior for accepting a stationary phase, a particulate stationary phase material packed within the nanocolumn, and an in situ frit within the nanocolumn, and adjacent to and integral with the stationary phase material. The in situ frit comprises an intimate mixture of particles of a stationary phase material and a polymeric network of cross-linked poly(diorganosiloxane) and particles of stationary phase material suspended in the network. The accepting means is capable of holding the nanocolumn in a configuration in which the nanocolumn is operatively connected to either a detecting means or an introducing means.

The detecting means is operatively connected to the nanocolumn and is capable of measuring physicochemical properties (light absorption/emission, conductivity, etc.), and examples include detectors such as those commonly used as HPLC detectors. Such detectors measure, e.g., refractive index, UV/Vis absorption or emission (at a fixed wavelength or variable wavelength), fluorescence (e.g., with a laser source), conductivity, molecular mass (by mass-spectrometry), and evaporative light scattering. Optical detectors are used frequently in liquid chromatographic systems. In these systems, the detector passes a beam of light through the flowing column effluent as it passes through a low volume flowcell. The variations in light intensity caused by UV absorption, fluorescence emission, or change in refractive index (depending on the type of detector used) from the sample components passing through the cell, are monitored as changes in the output voltage. These voltage changes are recorded on a strip chart recorder and frequently are fed into an integrator or computer to provide retention time and peak area data. A commonly used detector is an ultraviolet absorption detector. A variable wavelength detector of this type operates at about 190 nm to about 460 nm (or even about 600 nm).

The introducing means is operatively connected to the nanocolumn and is capable of conducting a liquid into the nanocolumn. Injectors and pumps are the most common introducing means used in liquid chromatography. A simplest method of sample introduction is to use an injection valve, although automatic sampling devices may be incorporated where sample introduction is done with the help of autosamplers and microprocessors. In liquid chromatography, liquid samples may be injected directly and solid samples need only be dissolved in an appropriate solvent. The solvent need not be the mobile phase, but frequently it is chosen to avoid detector, column, or component interference. Injectors for liquid chromatographic systems should provide the possibility of injecting a small volume liquid sample with high reproducibility and under high pressure. They should also produce minimum band broadening and minimize possible flow disturbances. An example of a sampling device is the microsampling injector valve. Because of their superior characteristics, valves such as the Rheodyne injector are very common, because these devices allow samples to be introduced reproducibly into pressurized columns without significant interruption of flow, even at elevated temperatures, and with injection volumes as small as 60 nL.

Examples of pumping means include high pressure pumps that are able to force solvents through packed stationary phase beds. Smaller bed particles are narrower bore columns require higher pressures. Ideally, such pumps have electronic feedback systems and multi-headed configurations that allow the pump to maintain a constant pressure. It is desirable to have an integrated degassing system, either helium purging, or better vacuum degassing.

Furthermore, the invention relates to a chromatography device prepared by the steps of providing a nanocolumn having a cylindrical interior for accepting a stationary phase, and forming a stationary phase within the nanocolumn. Such a stationary phase may comprise a particulate stationary phase material, and an in situ frit adjacent to and integral with the stationary phase material, wherein the in situ frit comprises an intimate mixture of particles of a stationary phase material and a polymeric network of cross-linked poly(diorganosiloxane) and the particles are suspended in the network.

One of the most fundamental tests of frit performance is its ability to withstand typical pressures encountered in HPLC separations (approx. 2700 psi). The in situ frits of the present invention are able to withstand higher pressures in nanocolumns. As noted above, the strength of an in situ frit may be fortified by sintering thus allowing even higher pressures. An in situ frit of the invention is usually capable of physically withstanding a pressure of at least about 1,000 psi applied to a liquid flowing through the stationary phase. In other embodiments, an in situ frit ia capable of physically withstanding chromatography pressures of at least about 10,000 psi applied to a liquid flowing through the stationary phase. In yet another embodiment, an in situ frit of the invention is capable of physically withstanding chromatography pressures of at least about 20,000 psi applied to a liquid flowing through the stationary phase.

Typically, an in situ frit is about 0.25 mm to about 2.5 mm in length, and may be about 0.5 mm to about 1.0 mm in length.

Also, an in situ frit is usually located at an end of the packed bed within the nanocolumn, either as an outlet frit or an inlet frit for a chromatography device.

As exemplified below, an in situ frit of the invention may have a tailing factor less than or equal to 2.3.

Methods of column packing are generally known in the art, see, e.g., Colon, et al., *J. Chromatog.* 887, 43 (2000), and depend principally on the mechanical strength of the packing, its particle size and particle size distribution, and the diameter of the column to be packed. Conventional column packing methods, such as dry packing, typically used for particles greater than about 20 μm in diameter, are not useful for small capillary columns that typically have diameters in the range of tens of microns. For particles between 1 and 20 μm in diameter slurry techniques can be used. In slurry packing the particles that form the bed are suspended as a slurry in an appropriate liquid or liquid mixture. Many liquids or liquid mixtures can be used to prepare the slurry, the principal requirement being that the liquid thoroughly wet the packing particles and provide adequate dispersion of the packing material. The slurry is then pumped into the column under high pressure optionally with mechanical agitation, e.g., sonication.

Accordingly, the invention relates to a method of making a chromatography device comprising the steps of a) providing a nanocolumn having a cylindrical interior for accepting a stationary phase, and b) forming a stationary phase within said nanocolumn, wherein said stationary phase comprises i) a particulate stationary phase material; and ii) an in situ frit adjacent to and integral with said stationary phase material, wherein said in situ frit comprises an intimate mixture of particles of a stationary phase material and a polymeric network of cross-linked poly(diorganosiloxane), and wherein said particles are suspended in said network. The step of "forming a stationary phase" may comprise the steps of a) preparing a mixture of said stationary phase material a solvent, and synthetic precursors of cross-linked poly(diorganosiloxane);

b) introducing said mixture prepared in step (a) into an end of said nanocolumn;

c) allowing the solvent to evaporate at room temperature;

d) curing the dried mixture by heating the nanocolumn and the mixture therein to a temperature of between about 70° C. to about 150° C. for a period of time ranging from about 0.5 hours to about 3 hours to thereby produce an in situ frit; and e) optionally sintering the in situ frit by heating the nanocolumn and the in situ frit therein to a temperature of between about 250° C. and about 350° C. for a period of time ranging from about 5 seconds to about 30 second.

Likewise, the invention discloses a method of making a chromatography device comprising the steps of a) preparing a mixture of a stationary phase material, a solvent, and polymer reagents that produce cross-linked poly(diorganosiloxane);

b) introducing said mixture prepared in step (a) into an end of said nanocolumn;

c) allowing the solvent to evaporate at room temperature;

d) curing the dried mixture by heating the nanocolumn and the mixture therein to a temperature of between about 70° C. to about 150° C. for a period of time ranging from about 0.5 hours to about 3 hours to thereby produce an in situ frit; and e) optionally sintering the in situ frit by heating the nanocolumn and the in situ frit therein to a temperature of between about 250° C. and about 350° C. for a period of time ranging from about 5 seconds to about 30 second.

Although the polymer may cross-link, i.e., "cure," without any further intervention, the curing step may comprise an additional step of heating the mixture to a temperature of between about 20° C. to about 40° C. for a period of time ranging from about 5 hours to about 35 hours, followed directly by heating the mixture to a temperature of between about 70° C. to about 150° C. for a period of time ranging from about 0.5 hours to about 3 hours. Alternatively, the curing step may comprise heating the mixture to room temperature for a period of about one day, followed by heating the mixture to a temperature of about 110° C. for a period of time of about 2 hours. Similarly, the sintering step may comprise heating the mixture to a temperature of between about 250° C. and about 350° C. for a period of time ranging from about 5 seconds to about 30 second; especially in embodiments in which the diameter of the in situ frit is greater than about 30 µm. Furthermore, the sintering step may comprise heating the mixture to a temperature of about 300° C. for a period of time of about 15 second; particularly when the diameter of the in situ frit is greater than about 30 µm. Another protocol entails letting the initial mixture stand at 25° C. for about 24 hours or heating the mixture at 40 to 150° C.

The present invention also relates to methods of using the chromatography devices and materials described herein. For example, the invention pertains to an analytical method of separating components of a mixture comprising a step of contacting the mixture with a column chromatography device of the invention. Similarly, the invention also covers a separations instrument comprising a column chromatography device of the invention. Additionally, the inventions discloses methods of analyzing components of a mixture comprising a step of contacting such a mixture with a column chromatography device of the invention, as well as methods of separating components of a mixture comprising a step of contacting such a mixture with a column chromatography device of the invention.

Furthermore, the instant application pertains to a separations instrument comprising a column chromatography device of the invention, such as a CE, nanoLC, or CEC instrument. Such instruments may comprise a pumping means for moving liquid through the column chromatography device, and a detecting means for analyzing the column chromatography device effluent.

EXAMPLES

Those skilled in the art will recognize, or be able to ascertain using no more than routine experimentation, numerous equivalents to the specific procedures, embodiments, claims, and examples described herein. Such equivalents were considered to be within the scope of this invention and are covered by the claims appended hereto. The contents of all references, issued patents, and published patent applications cited throughout this application are hereby incorporated by reference. The invention is further illustrated by the following examples, which should not be construed as further limiting.

Example 1

Synthesis of Column

Beds of 3.5 µm Symmetry C18 stationary phase material were chemically immobilized using poly(dimethylsiloxane) (PDMS) as a "nanoglue" to hold the particles together. A New Objective Integra frit column (75 µm fused silica capillary, New Objective, Inc., Woburn, Mass., USA) was packed using a 5 mg/mL of 3.5 µm Symmetry C18 particles (Waters Corporation, Milford, Mass., USA) in acetone. After packing to a bed length of 12 cm, the column was removed and allowed to dry under ambient conditions. The column was then carefully cut into three 4 cm lengths of packed capillary and the Integra frit (New Objective, Inc., Woburn, Mass., USA) was removed from the terminus of the last section. Three solutions of 1%, 5%, and 10% PDMS in 1,4-dioxane were prepared by sequentially adding the monomers of the two component PDMS Sylgard 184 kit (Dow Corning Corporation, Midland, Mich., USA) in a 10:1 monomer A:monomer B ratio. The three sections of packed capillary were then dipped in to one of the aforementioned PDMS mixtures for 10 s, the ends were blotted, and inserted through the septa of a 1 mL sample vial with the dipped end pointing out. The samples were placed in a 110° C. oven for 1.5 h to cure. After the curing period, the samples were allowed to cool to room temperature before handling.

Example 2

Synthesis of Column

An alternative method to that of Example 1 includes a step of immediate sintering of a slurry of Symmetry $C_{18}$ particles in a 5% PDMS solution, which had been drawn into the capillary. A 20 cm length of 75 μm i.d. fused silica capillary was dipped into a 100 mg/mL slurry of 3.5 μm Symmetry $C_{18}$ material in 5% PDMS in ethyl acetate for 3 s. During this time 1 cm of the capillary was filled with slurry solution. The 1 cm section of the filled capillary was then placed into the resistive heating coil of an Innovatech frit making device (InnovaTech, Stevenage, Hertfordshire, United Kingdom), which was used to heat the area to about 350° C. Similar results may be achieved with a heated wire cutter or even with a lighted candle.

Example 3

Synthesis of Column

Figure 2A:
FIG. 2 presents two SEM images at magnifications of (A) 500 and (B) 2500 of a sintered PDMS frit prepared according to Example 3.

In yet another example, the slurry may be drawn into a capillary, the PDMS cured, and then sintered. A 20 cm length of 75 μm i.d. fused silica capillary was dipped into a 100 mg/mL slurry of 3.5 μm Symmetry $C_{18}$ material in 5% PDMS in ethyl acetate. The capillary was allowed to dry in ambient conditions for 3 h, and was then placed in a 110° C. oven overnight. The following morning, the column frit was sintered in place using the Innovatech frit making device, discussed in Example 2. FIG. 2 presents two SEM images at magnifications of (A) 500 and (B) 2500 of a sintered PDMS frit prepared according to this example.

Example 4

Pressure Testing of Frits

All fabricated frits were pressure tested by connection to an Alliance HT (Waters Corporation, Milford Mass., USA) adapted to handle nano-flow by using a 2000:1 post-injector split ratio. Evidence for frit rupture was monitored visually, and the results are discussed below. The flow rate was ~280 nL/min with 100% water at pressures around 2700 psi.

Example 5

Packing of Fritted Columns

Columns with PDMS frits were packed similarly to Integra frit columns. A 3-5 mg/mL 5 mg/mL slurry of Symmetry $C_{18}$ material in acetone was used in all cases at a packing pressure of 1,000-10,000 psi.

Example 6

SEM Analysis of Frits

Figure 1B:
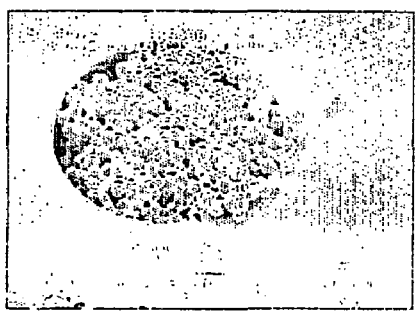
Figure 1C:

After preparation of a set of three PDMS frits according to Example 1, the samples were cleaved to expose a fresh area of immobilized bed, and submitted for SEM analysis to determine the effect of PDMS solution concentration on frit morphology. FIG. 1 presents three SEM images of frits formed with 1%, 5%, and 10% PDMS solutions in 1,4-dioxane.

FIG. 1 illustrates the adhesion of the silica particles to each other. This is especially apparent in the case of the 10% PDMS solution where poor definition of individual particles is observed. Since the particles from the 5% PDMS study appeared to be adhered well enough without losing definition of the particles themselves, this solution concentration was used in subsequent sintering protocols.

Figure 2B:
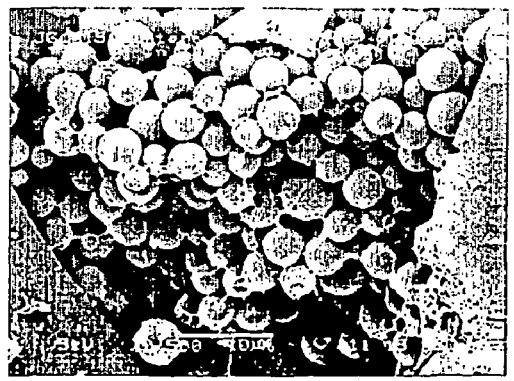

Particle connectivity is readily observed from FIG. 2B, as one can see thin grey "threads" of PDMS holding particles together, which were not observed in SEM images of unsintered frits.

Example 7

Effect of Pressure on Frits

Frits fabricated according to Example 1 ruptured at 1200 psi, however frits prepared according to Examples 2 and 3 did not rupture at the maximum pressure used in this study (~2700 psi). In a subsequent test, ten frits were similarly prepared and tested. The average rupture pressure was 16,000 psi. When the columns were packed, the rupture pressure was 42,000 psi.

Example 8

Chromatographic Performance of Column

Figure 3:
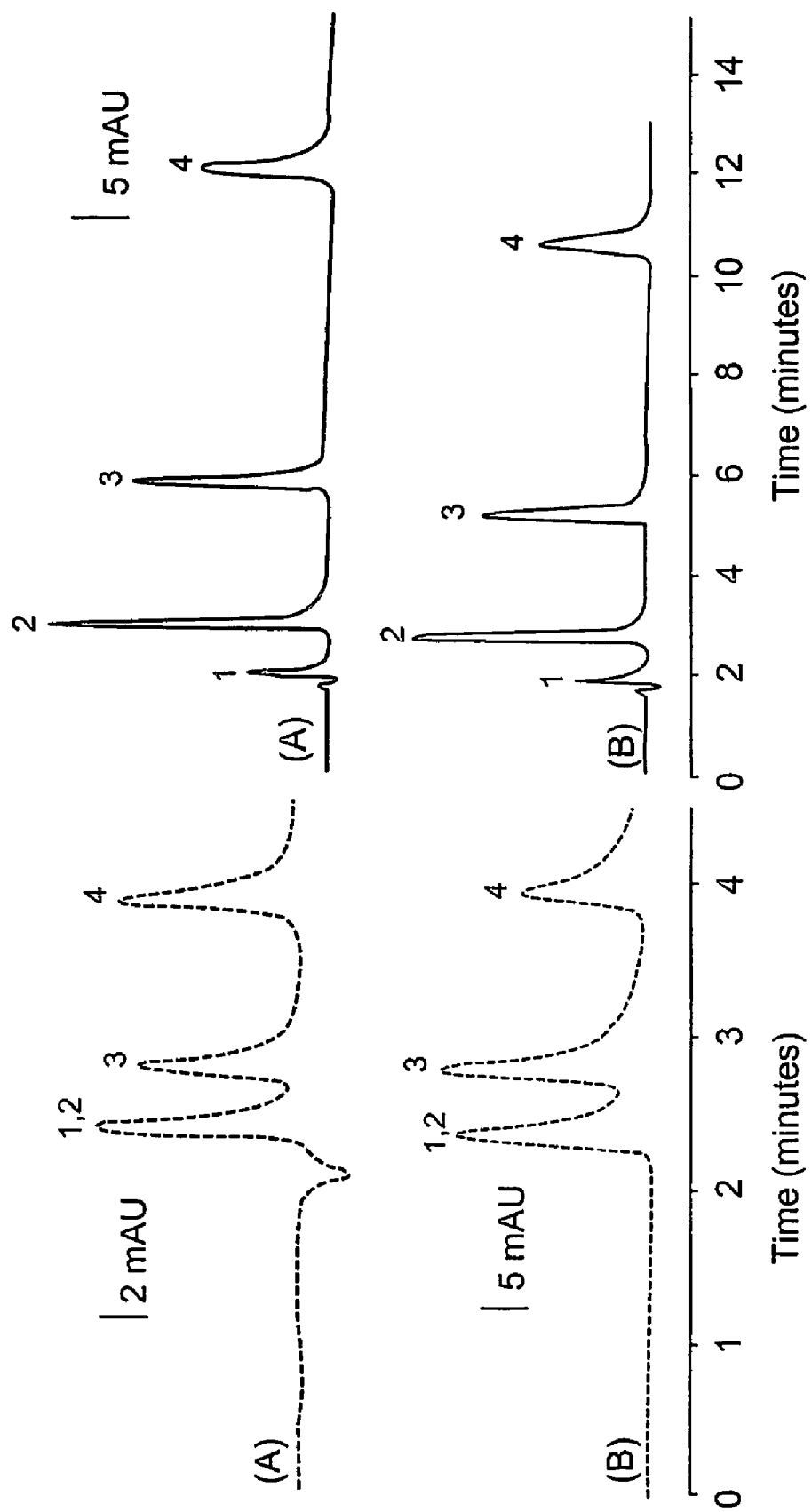
FIG. 3: (LeftPanel) shows separation of acetone (1), ethyl paraben (2), butyl paraben (3),and naphthalene (4) on (A) an Integra frit column and (B) a PDMS frit column prepared according to Example 2; (Right Panel) shows separation of acetone (1), ethyl paraben (2), butyl paraben (3), and naphthalene (4) on (A) an Integra frit column and (B) a PDMS frit column prepared according to Example 3.

PDMS frits prepared according to Examples 2 and 3 were evaluated using a standard mixture of four small molecules and compared to a similar separation on an equivalent Integra frit packed capillary column. Bed lengths of all columns were ~10 cm. The mobile phase was 60:40 ACN:$H_2O$. FIG. 3 shows sets of comparative chromatograms for PDMS frits prepared according to Examples 2 and 3, respectively.

In the case of frits prepared according to Example 2, greater peak tailing is observed in comparison to the Integra frit column. However, columns prepared using Example 3 performed extremely well, and even had better USP tailing factors than the Integra frit column. Frits made using Example 3 not only are robust under pressure, they also have comparable performance to a commercial frit.

Example 9

Chromatographic Performance of Column

New Objective IntegraFrit™ 75 μm i.d. fused silica capillaries were slurry packed at 1000 psi with 5 mg/mL Symmetry $C_{18}$ (3.5 μm particle size; 100 Å pore size) in acetone. PDMS exit frits were prepared by drawing a 1 cm plug of slurry consisting of 100 mg/mL 3.5 μm Symmetry $C_{18}$ material in 5% PDMS ethyl acetate solution into a 20 cm length 75 μm silica capillary. The ethyl acetate was allowed to evaporate under ambient conditions for 3 hours, and then the capillary was placed into a 110° C. oven for 8 h. The frit was then secured by sintering at ~300° C. The chromatographic performance of both IntegraFrit™ and PDMS frit nanocolumns thus prepared were compared in the separation of a mixture comprising the following components:

| | |
|---|---|
| Uracil | 16 μg/mL |
| Propanolol | 400 μg/mL |
| Butyl Paraben | 20 μg/mL |
| Dipropyl Phthalate | 340 μg/mL |
| Naphthalene | 60 μg/mL |
| Acenaphthene | 200 μg/mL |
| Amitriptyline | 100 μg/mL |

Figure 4:
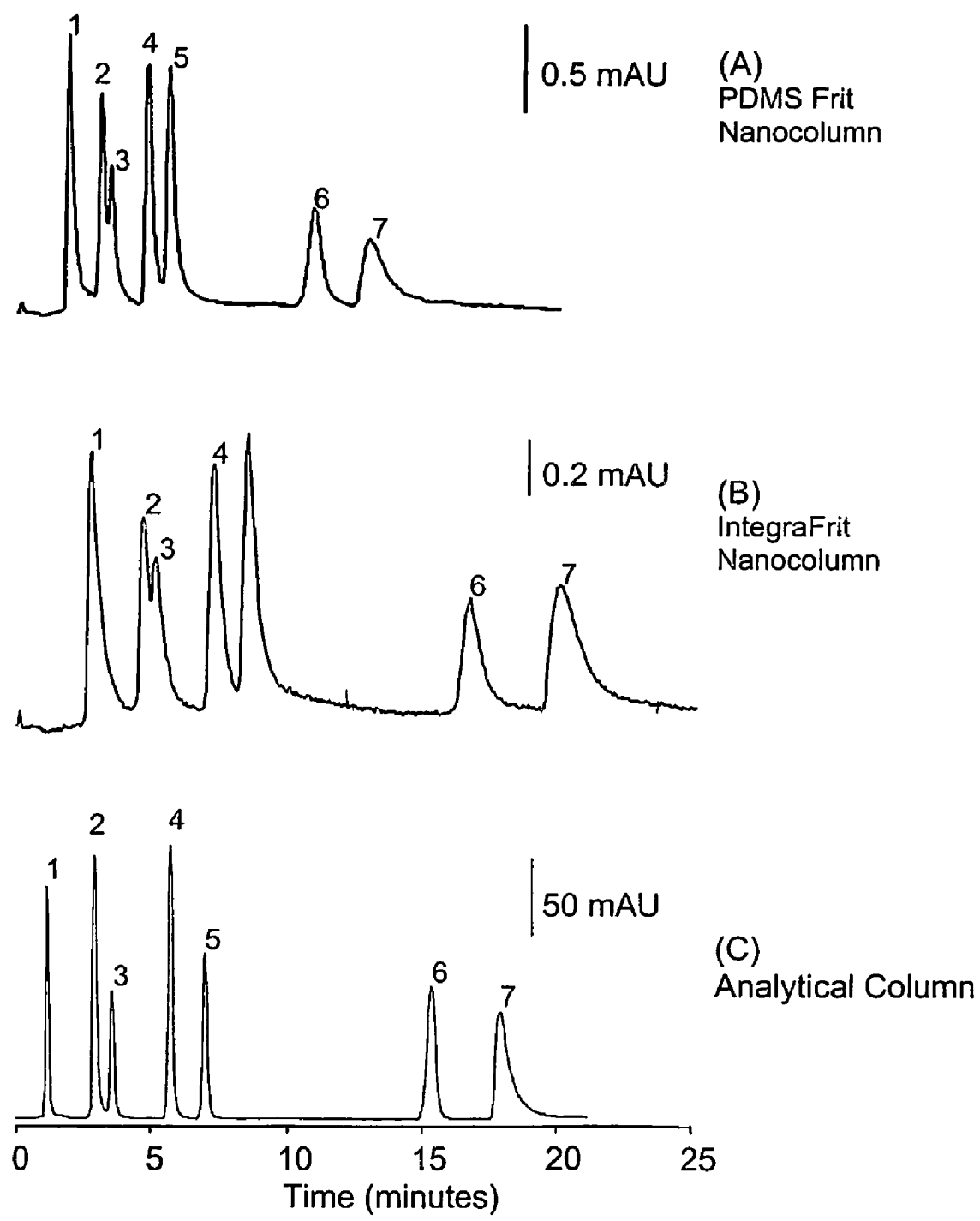
FIG. 4 shows separation of batch test mix on (A) a nanocolumn (75 μm×100 mm) with a PDMS frit, (B) a nanocolumn (75 μm×100 mm) with an IntegraFrit™, and (C) an analytical column (2.1 mm×100 mm).

In all separations involving the batch test mix, the mobile phase consisted of 65:35 methanol:20 mM $K_2HPO_4/KH_2PO_4$ (pH=7.00) at a flow rate of 250 μL/min for the analytical column and 458 nL/min for the nanocolumns. Analytes were detected by fluorescence at 254 nm, and the chromatograms are represented in FIGS. 3 and 4.

Nanocolumns prepared with a PDMS frit had an acceptable tailing factor of 2.09 for amitryptiline, whereas Integra Frit™ nanocolumns had a tailing factor of 2.38. (The tailing factor of amitryptiline is an indicator of the amount of residual silanol groups present on the stationary phase.) The frit was observed to have no effect on peak position and shape. After chromatographic evaluation, the flow in the nanocolumn was reversed to ascertain the stability of the inlet frit. At an operating back pressure of ~2900 psi, the inlet frit did not rupture, thus indicating that column back-washing is possible.

Example 10

Chromatographic Performance of In Situ Frits Prepared with and without PDMS

Attempts to sinter Xterra® stationary phase materials (Waters Corporation, Milford, Mass., USA) according to the methods herein in the absense of a poly(dimethylsiloxane) resulted in the organic groups attached to the silica surface being thermally removed, thereby leaving bare silanol groups exposed. such silanol groups are known to contribute to peak tailing, and this effect was manifested as measured tailing factors around 2.0. Using the same conditions as in Example 9, chromatographic analysis of a test solution containing amitriptyline indicated that residual silanol groups were produced by sintering of the stationary phase material. However, when identical in situ frits were prepared using the PDMS techniques described herein with Xterra or Sunfire materials, no increase in tailing was observed upon sintering.

Incorporation By Reference

The entire contents of all patents, published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims. The contents of all references, issued patents, and published patent applications cited throughout this application are hereby incorporated by reference.

The invention claimed is:

1. An in situ frit for immobilizing a stationary phase material in a chromatography nanocolumn comprising an intimate mixture of particles comprising a stationary phase material and a polymeric network comprising cross-linked poly(diorganosiloxane), wherein said particles are suspended in said network.

2. A medium for molecular separations comprising
  a) a particulate stationary phase material; and
  b) an in situ frit adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network.

3. A column chromatography device comprising
  a) a nanocolumn having a cylindrical interior for accepting a stationary phase;
  b) a particulate stationary phase material packed within said nanocolumn; and
  c) an in situ frit within said nanocolumn, and adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network.

4. A chromatography device prepared by the steps of providing a nanocolumn having a cylindrical interior for accepting a stationary phase, and forming a stationary phase within said nanocolumn, wherein said stationary phase comprises
  a) a particulate stationary phase material; and
  b) an in situ frit adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network.

5. The column chromatography device of claim 3, wherein said poly(diorganosiloxane) is a polymer having a repeat unit of the formula —(—$R^1R^2SiO$—)—, wherein $R^1$ and $R^2$ are independently hydrogen, a $C_1$-$C_{18}$ aliphatic group, an aromatic group, or a cross-linking group.

6. The column chromatography device of claim 3, wherein said poly(diorganosiloxane) is a polymer having the formula (—$R^1R^2SiO$—)$_n$, wherein $R^1$ and $R^2$ are independently hydrogen, a $C_1$-$C_{18}$ aliphatic group, an aromatic group, or a cross-linking group, and n represents the number of repeat units.

7. The column chromatography device of claim 6, wherein said cross-linking group is a hydrocarbon group containing a polymerizable alkenyl group or a polymerized product thereof.

8. The column chromatography device of claim 7, wherein said cross-linking group is a vinyl group or a styryl group or a polymerized product thereof.

9. The column chromatography device of claim 6, wherein said aliphatic group is a straight or branched-chain alkyl or cycloalkyl group.

10. The column chromatography device of claim 9, wherein said aliphatic group is a $C_1$-$C_6$ alkyl group.

11. The column chromatography device of claim 10, wherein said aliphatic group is a methyl, ethyl, n-propyl, isopropyl, butyl, sec-butyl, or tert-butyl group.

12. The column chromatography device of claim 3, wherein said poly(diorganosiloxane) is selected from poly (dimethylsiloxane) polymers.

13. The column chromatography device of claim 3, wherein said cross-linked poly(diorganosiloxane) is selected from the group consisting of cross-linked poly(dimethylsiloxane) polymers.

14. The column chromatography device of claim 3, wherein said cross-linked poly(diorganosiloxane) is produced by the reaction of a polymer reagent comprising vinyl-substituted dimethyl siloxane.

15. The column chromatography device of claim 14, wherein said vinyl-substituted dimethyl siloxane is dimethylvinyl-terminated dimethyl siloxane.

16. The column chromatography device of claim 14, wherein said reaction comprises a further polymer reagent selected from the group consisting of dimethyl siloxane, methylhydrogen siloxane, dimethylvinylated silica, trimethylated silica, tetramethyl tetravinyl cyclotetrasiloxane, and tetra(trimethylsiloxy) silane.

17. The column chromatography device of claim 16, wherein said dimethyl siloxane or methylhydrogen siloxane has an average molecular weight of about 10 Da to about 10,000.

18. The column chromatography device of claim 17, wherein said dimethyl siloxane or methylhydrogen siloxane has an average molecular weight of about 100 Da to about 1,000.

19. The column chromatography device of claim 14, wherein said vinyl-substituted dimethyl siloxane has an average molecular weight of about 500 Da to about 100,000 Da.

20. The column chromatography device of claim 19, wherein said vinyl-substituted dimethyl siloxane has an average molecular weight of about 10,000 Da to about 40,000 Da.

21. The column chromatography device of claim 3, wherein said mixture has been cured in situ by heating.

22. The column chromatography device of claim 3, wherein said mixture has been further immobilized by sintering.

23. The column chromatography device of claim 21, wherein said curing step comprises heating the mixture to a temperature of between about 25° C. and about 150° C. for a period of time ranging from about 1hour to about 48 hours.

24. The column chromatography device of claim 3, wherein the particles of said stationary phase material have an average size/diameter of about 0.5 μm to about 10 μm.

25. The column chromatography device of claim 3, wherein said stationary phase material is porous.

26. The column chromatography device of claim 3, wherein said stationary phase material is non-porous.

27. The column chromatography device of claim 3, wherein said stationary phase material has an average pore diameter of about 70 Å to about 300 Å.

28. The column chromatography device of claim 3, wherein said stationary phase material has a specific surface area of about 170 $m^2$/g to about 250 $m^2$/g.

29. The column chromatography device of claim 3, wherein said stationary phase material has a specific pore volumes of about 0.2 $cm^3$/g to about 1.5 $cm^3$/g.

30. The column chromatography device of claim 3, wherein said particulate stationary phase material is alumina, silica, titanium oxide, zirconium oxide, a ceramic material, an organic polymer, or a mixture thereof.

31. The column chromatography device of claim 3, wherein said stationary phase material has been bonded with a surface modifier.

32. The column chromatography device of claim 31, wherein said surface modifier is selected from the group consisting of alkyl group, alkenyl group, alkynyl group, aryl group, cyano group, amino group, diol group, nitro group, ester group, or an alkyl or aryl group containing an embedded polar functionality.

33. The column chromatography device of claim 32, wherein said alkyl group is selected from the group consisting methyl, ethyl, propyl, isopropyl, butyl, Cert-butyl, sec-butyl, pentyl, isopentyl, hexyl, cyclohexyl, octyl, and octadecyl groups.

34. The column chromatography device of claim 3, wherein said stationary phase material is alkyl-bonded, phenyl-bonded, cyano-bonded, diol-bonded, or amino-bonded silica, or a mixture thereof.

35. The column chromatography device of claim 3, wherein said stationary phase material comprises porous inorganic/organic hybrid particles.

36. The column chromatography device of claim 3, wherein said stationary phase material comprises porous inorganic/organic hybrid particles having the formula $SiO_2/(R^2_p R^4_q SiO_t)_n$ or $SiO_2/[R^6(R^2_r SiO_t)_m]_n$, wherein $R^2$ and $R^4$ are independently $C_1$-$C_{18}$ aliphatic, styryl, vinyl, propanol, or aromatic groups, $R^6$ is a substituted or unsubstituted $C_1$-$C_{18}$ alkylene, alkenylene, alkynylene or arylene group bridging two or more silicon atoms, p and q are 0, 1 or 2, provided that p+q =1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1.

37. The column chromatography device of claim 3, wherein said nanocolumn is a capillary.

38. The column chromatography device of claim 3, wherein the inner diameter of said nanocolumn is about 10 μm to about 1.0 mm.

39. The column chromatography device of claim 38, wherein said inner diameter is about 25 μM to about 320 μm.

40. The column chromatography device of claim 3, wherein said nanocolumn is made of fused silica, glass, stainless steel, a polymer, a ceramic, or a mixture thereof.

41. The column chromatography device of claim 3, wherein said in situ frit is about 0.25 mm to about 2.5 mm in length.

42. The column chromatography device of claim 41, wherein said in situ frit is about 0.5 mm to about 1.0 mm in length.

43. The column chromatography device of claim 3, wherein said in situ frit is located at an end of the packed bed within said nanocolumn.

44. The column chromatography device of claim 3, wherein said in situ frit is an outlet frit for a chromatography device.

45. The column chromatography device of claim 3, wherein said in situ frit is an inlet frit for a chromatography device.

46. The column chromatography device of claim 3, wherein said in situ frit capable of physically withstanding a pressure of at least about 1,000 psi applied to a liquid flowing through the stationary phase.

47. The column chromatography device of claim 3, wherein said in situ frit capable of physically withstanding chromatography pressures of at least about 10,000 psi applied to a liquid flowing through the stationary phase.

48. The column chromatography device of claim 3, wherein said in situ frit capable of physically withstanding chromatography pressures of at least about 20,000 psi applied to a liquid flowing through the stationary phase.

49. The column chromatography device of claim 3, wherein said in situ frit has a tailing factor less than or equal to 2.3.

50. A method of making a chromatography device comprising the steps of
   a) providing a nanocolumn having a cylindrical interior for accepting a stationary phase;
   b) forming a stationary phase within said nanocolumn, wherein said stationary phase comprises
   i) a particulate stationary phase material; and
   ii) an in situ frit adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network;
   c) curing the stationary phase within said nanocolumn; and
   d) optionally sintering the stationary phase within said nanocolumn.

51. A separations instrument comprising a (i) column chromatography device and at least one component selected from a (ii) detecting means, an (iii) introducing means, or an (iv) accepting means, wherein (i) said column chromatography device comprises
   a) a nanocolumn having a cylindrical interior for accepting a stationary phase,
   b) a particulate stationary phase material packed within said nanocolumn, and
   c) an in situ frit within said nanocolumn, and adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network;
(ii) said detecting means is operatively connected to said nanocolumn and is capable of measuring physicochemical properties; and
(iii) said introducing means is operatively connected to said nanocolumn and is capable of conducting a liquid into said nanocolumn; and
(iv) said accepting means is capable of holding said nanocolumn in a configuration in which the nanocolumn is operatively connected to either a detecting means or an introducing means.

52. A separations instrument comprising a column chromatography device comprising
   a) a nanocolumn having a cylindrical interior for accepting a stationary phase;
   b) a particulate stationary phase material packed within said nanocolumn; and
   c) an in situ frit within said nanocolumn, and adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network.

53. An analytical method of separating components of a mixture comprising a step of contacting said mixture with a column chromatography device comprising
   a) a nanocolumn having a cylindrical interior for accepting a stationary phase;
   b) a particulate stationary phase material packed within said nanocolumn; and
   c) an in situ frit within said nanocolumn, and adjacent to and integral with said stationary phase material, wherein said in situ frit comprises an intimate mixture of particles comprising a stationary phase material and a polymeric network comprising cross-linked poly(diorganosiloxane), and wherein said particles are suspended in said network.

54. A method of analyzing components of a mixture comprising a step of contacting said mixture with a column chromatography device according to claim 3.

55. A method of separating components of a mixture comprising a step of contacting said mixture with a column chromatography device according to claim 3.

56. The column chromatography device of claim 3, wherein said intimate mixture is a 10:1 (w/w) composition of particles of stationary phase material and a polymeric network of cross-linked poly(diorganosiloxane) in a ratio of about 10:1 to about 1000:1 stationary phase material to polymer by weight.

57. The column chromatography device of claim 56, wherein said ratio is about 10:1 to about 100:1 stationary phase material to polymer by weight.

58. The column chromatography device of claim 3, wherein the particles of said stationary phase material are approximately spherical.

59. A method of making a chromatography device comprising the steps of
   a) preparing a mixture of a stationary phase material, a solvent, and polymer reagents that produce cross-linked poly(diorganosiloxane);
   b) introducing said mixture prepared in step (a) into an end of said nanocolumn;
   c) allowing the solvent to evaporate at room temperature;
   d) curing the dried mixture by heating the nanocolumn and the mixture therein to a temperature of between about 70° C. to about 150° C. for a period of time ranging from about 0.5 hours to about 3 hours to thereby produce an in situ frit; and
   e) optionally sintering the in situ frit by heating the nanocolumn and the in situ frit therein to a temperature of between about 250° C. and about 350° C. for a period of time ranging from about 5 seconds to about 30 second.

60. The method of claim 50, wherein said step of forming a stationary phase comprises the steps of:
   a) preparing a mixture of said stationary phase material, a solvent, and synthetic precursors of cross-linked poly(diorganosiloxane);
   b) introducing said mixture prepared in step (a) into an end of said nanocolumn;
   c) allowing the solvent to evaporate at room temperature;
   d) curing the dried mixture by heating the nanocolumn and the mixture therein to a temperature of between about 70° C. to about 150° C. for a period of time ranging from about 0.5 hours to about 3 hours to thereby produce an in situ frit; and
   e) optionally sintering the in situ frit by heating the nanocolumn and the in situ frit therein to a temperature of between about 250° C. and about 350° C. for a period of time ranging from about 5 seconds to about 30 seconds.

61. The method of claim 50, wherein said curing step comprises heating the mixture to a temperature of between about 20° C. to about 40° C. for a period of time ranging from about 5 hours to about 35 hours, followed directly by heating the mixture to a temperature of between about 70° C. to about 150° C. for a period of time ranging from about 0.5 hours to about 3 hours.

62. The method of claim 50, wherein said curing step comprises heating the mixture to room temperature for a period of about one day, followed by heating the mixture to a temperature of about 110° C. for a period of time of about 2 hours.

63. The method of claim 50, wherein said sintering step comprises heating the mixture to a temperature of between about 250° C. and about 350° C. for a period of time ranging from about 5 seconds to about 30 seconds.

64. The method of claim 63, wherein the diameter of said in situ frit is greater than about 30 μm.

65. The method of claim 50, wherein said sintering step comprises heating the mixture to a temperature of about 300° C. for a period of time of about 15 seconds.

66. The method of claim 63, wherein the diameter of said in situ frit is greater than about 30 μm.

67. The method of claim 50, wherein said poly(diorganosiloxane) is a polymer having a repeat unit of the formula —($—R^1R^2SiO—$)—, wherein $R^1$ and $R^2$ are independently hydrogen, a $C_1$-$C_{18}$ aliphatic group, an aromatic group, or a cross-linking group.

68. The method of claim 50, wherein said poly(diorganosiloxane) is a polymer having the formula ($—R^1R^2SiO—$)$_n$, wherein $R^1$ and $R^2$ are independently hydrogen, a $C_1$-$C_{18}$ aliphatic group, an aromatic group, or a cross-linking group, and n represents the number of repeat units.

69. The method of claim 67, wherein said cross-linking group is a hydrocarbon group containing a polymerizable alkenyl group or a polymerized product thereof.

70. The method of claim 69, wherein said cross-linking group is a vinyl group or a styryl group or a polymerized product thereof.

71. The method of claim 68, wherein said aliphatic group is a straight or branched-chain alkyl or cycloalkyl group.

72. The method of claim 68, wherein said aliphatic group is a $C_1$-$C_6$ alkyl group.

73. The method of claim 72, wherein said aliphatic group is a methyl, ethyl, n-propyl, isopropyl, butyl, sec-butyl, or tert-butyl group.

74. The method of claim 50, wherein said poly(diorganosiloxane) is selected from poly(dimethylsiloxane) polymers.

75. The method of claim 50, wherein said cross-linked poly(diorganosiloxane) is selected from the group consisting of cross-linked poly(dimethylsiloxane) polymers.

76. The method of claim 50, wherein said cross-linked poly(diorganosiloxane) is produced by the reaction of a polymer reagent comprising vinyl-substituted dimethyl siloxane.

77. The method of claim 76, wherein said vinyl-substituted dimethyl siloxane is dimethylvinyl-terminated dimethyl siloxane.

78. The method of claim 76, wherein said reaction comprises a further polymer reagent selected from the group consisting of dimethyl siloxane, methylhydrogen siloxane, dimethylvinylated silica, trimethylated silica, tetramethyl tetravinyl cyclotetrasiloxane, and tetra(trimethylsiloxy) silane.

79. The method of claim 78, wherein said dimethyl siloxane or methylhydrogen siloxane has an average molecular weight of about 10 Da to about 10,000.

80. The method of claim 79, wherein said dimethyl siloxane or methylhydrogen siloxane has an average molecular weight of about 100 Da to about 1,000.

81. The method of claim 76, wherein said vinyl-substituted dimethyl siloxane has an average molecular weight of about 500 Da to about 100,000 Da.

82. The method of claim 81, wherein said vinyl-substituted dimethyl siloxane has an average molecular weight of about 10,000 Da to about 40,000 Da.

83. The method of claim 50, wherein said mixture has been cured in situ by heating.

84. The method of claim 50, wherein said mixture has been further immobilized by sintering.

85. The method of claim 50, wherein said curing step comprises heating the mixture to a temperature of between about 25° C. and about 150° C. for a period of time ranging from about 1 hour to about 48 hours.

86. The method of claim 50, wherein the particles of said stationary phase material have an average size/diameter of about 0.5 μm to about 10 μm.

87. The method of claim 50, wherein said stationary phase material is porous.

88. The method of claim 50, wherein said stationary phase material is non-porous.

89. The method of claim 50, wherein said stationary phase material has an average pore diameter of about 70 Å to about 300 Å.

90. The method of claim 50, wherein said stationary phase material has a specific surface area of about 170 m$^2$/g to about 250 m$^2$/g.

91. The method of claim 50, wherein said stationary phase material has a specific pore volumes of about 0.2 cm$^3$/g to about 1.5 cm$^3$/g.

92. The method of claim 50, wherein the particulate stationary phase material is alumina, silica, titanium oxide, zirconium oxide, a ceramic material, an organic polymer, or a mixture thereof.

93. The method of claim 50, wherein said stationary phase material has been bonded with a surface modifier.

94. The method of claim 93, wherein said surface modifier is selected from the group consisting of alkyl group, alkenyl group, alkynyl group, aryl group, cyano group, amino group, diol group, nitro group, ester group, or an alkyl or aryl group containing an embedded polar functionality.

95. The method of claim 94, wherein said alkyl group is selected from the group consisting methyl, ethyl, propyl, isopropyl, butyl, tert-butyl, sec-butyl, pentyl, isopentyl, hexyl, cyclohexyl, octyl, and octadecyl groups.

96. The method of claim 50, wherein said stationary phase material is alkyl-bonded, phenyl-bonded, cyano-bonded, diol-bonded, or amino-bonded silica, or a mixture thereof.

97. The method of claim 50, wherein said stationary phase material comprises porous inorganic/organic hybrid particles.

98. The method of claim 50, wherein said stationary phase material comprises porous inorganic/organic hybrid particles having the formula $SiO_2/(R^2_p R^4_q SiO_t)_n$ or $SiO_2/[R^6(R^2_r SiO_t)_m]_n$, wherein $R^2$ and $R^4$ are independently $C_1$-$C_{18}$ aliphatic, styryl, vinyl, propanol, or aromatic groups, $R^6$ is a substituted or unsubstituted $C_1$-$C_{18}$ alkylene, alkenylene, alkynylene or arylene group bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1.

99. The method of claim 50, wherein said nanocolumn is a capillary.

100. The method of claim 50, wherein the inner diameter of said nanocolumn is about 10 μm to about 1.0 mm.

101. The method of claim 50, wherein said inner diameter is about 25 μM to about 320 μm.

102. The method of claim 50, wherein said nanocolumn is made of fused silica, glass, stainless steel, a polymer, a ceramic, or a mixture thereof.

103. The method of claim 50, wherein said in situ frit is about 0.25 mm to about 2.5 mm in length.

104. The method of claim 103, wherein said frit is about 0.5 mm to about 1.0 mm in length.

105. The method of claim 50, wherein said in situ frit is located at an end of the packed bed within said nanocolumn.

106. The method of claim 50, wherein said in situ frit is an outlet frit for a chromatography device.

107. The method of claim 50, wherein said in situ frit is an inlet frit for a chromatography device.

108. The method of claim 50, wherein said in situ frit capable of physically withstanding a pressure of at least about 1,000 psi applied to a liquid flowing through the stationary phase.

109. The method of claim 50, wherein said in situ frit capable of physically withstanding chromatography pressures of at least about 10,000 psi applied to a liquid flowing through the stationary phase.

110. The method of claim 50, wherein said in situ frit capable of physically withstanding chromatography pressures of at least about 20,000 psi applied to a liquid flowing through the stationary phase.

111. The method of claim 50, wherein said in situ frit has a tailing factor less than or equal to 2.3.

112. A separations instrument comprising a column chromatography device according to claim 3.

113. The instrument of claim 112, wherein said instrument is a CE, nanoLC, or CEC instrument.

114. The instrument of claim 112, wherein said instrument comprises a pumping means for moving liquid through said column chromatography device, and a detecting means for analyzing the column chromatography device effluent.

115. A method of claim 50, wherein said intimate mixture is a 10:1 (w/w) composition of particles of stationary phase material and a polymeric network of cross-linked poly(diorganosiloxane) in a ratio of about 10:1 to about 1000:1 stationary phase material to polymer by weight.

116. The method of claim 115, wherein said ratio is about 10:1 to about 100:1 stationary phase material to polymer by weight.

117. A method of claim 50, wherein the particles of said stationary phase material are approximately spherical.

118. A method of claim 51, wherein said mixture prepared in step (a) contains sufficient amounts of stationary phase material, solvent, and polymer reagents to yield after curing in step (d) a 10:1 (w/w) composition of particles of stationary phase material and a polymeric network of cross-linked poly(diorganosiloxane) in a ratio of about 10:1 to about 1000:1 stationary phase material to polymer by weight.

119. The method of claim 118, wherein said ratio is about 10:1 to about 100:1 stationary phase material to polymer by weight.

120. The method of claim 50, wherein the particles of said stationary phase material are approximately spherical.

* * * * *